United States Patent
Rader et al.

(10) Patent No.: US 9,758,586 B2
(45) Date of Patent: Sep. 12, 2017

(54) CHIMERIC RABBIT/HUMAN ROR1 ANTIBODIES

(75) Inventors: Christoph Rader, Jupiter, FL (US); Jiahui Yang, Kunming (CN)

(73) Assignee: The United States of America, as represented by the Secretary, Department of Health and Human Services, Washington, DC (US)

(*) Notice: Subject to any disclaimer, the term of this patent is extended or adjusted under 35 U.S.C. 154(b) by 0 days.

(21) Appl. No.: 13/990,977

(22) PCT Filed: Nov. 30, 2011

(86) PCT No.: PCT/US2011/062670
§ 371 (c)(1),
(2), (4) Date: Jun. 7, 2013

(87) PCT Pub. No.: WO2012/075158
PCT Pub. Date: Jun. 7, 2012

(65) Prior Publication Data
US 2013/0251642 A1  Sep. 26, 2013

Related U.S. Application Data

(60) Provisional application No. 61/418,550, filed on Dec. 1, 2010.

(51) Int. Cl.
C07K 16/28 (2006.01)

(52) U.S. Cl.
CPC ...... C07K 16/2869 (2013.01); C07K 16/2857 (2013.01); C07K 2317/55 (2013.01); C07K 2317/624 (2013.01); C07K 2317/732 (2013.01); C07K 2317/734 (2013.01); C07K 2317/92 (2013.01)

(58) Field of Classification Search
CPC .................. C07K 16/2869; C07K 16/2857
See application file for complete search history.

(56) References Cited

U.S. PATENT DOCUMENTS

| | | | |
|---|---|---|---|
| 5,843,749 A | 12/1998 | Maisonpierre et al. | |
| 7,935,340 B2 * | 5/2011 | Garcia-Martinez et al. | 424/133.1 |
| 2007/0207510 A1 | 9/2007 | Kipps et al. | |
| 2008/0299136 A1 | 12/2008 | Ernst et al. | |
| 2010/0062005 A1 | 3/2010 | Kipps et al. | |
| 2011/0008347 A1 | 1/2011 | Ullrich et al. | |

FOREIGN PATENT DOCUMENTS

| | | |
|---|---|---|
| WO | WO 2005/100605 A1 | 10/2005 |
| WO | WO 2010/124188 A1 | 10/2010 |
| WO | WO 2011/159847 A2 | 12/2011 |

OTHER PUBLICATIONS

Baskar et al., "Unique cell surface expression of receptor tyrosine kinase ROR1 in human b-cell chronic lymphocytic leukemia," *Clin. Cancer Res.*, 14(2): 396-404 (2008).
Daneshmanesh et al., "Ror1, a cell surface receptor tyrosine kinase is expressed in chronic lymphocytic leukemia and may serve as a putative target for therapy," *Int. J. Cancer*, 123: 1190-1195 (2008).
European Patent Office, International Search Report in International Patent Application No. PCT/US2011/062670 (Feb. 23, 2012).
European Patent Office, Written Opinion in International Patent Application No. PCT/US2011/062670 (Feb. 23, 2012).
Fukuda et al., "Antisera induced by infusions of autologous Ad-CD154-leukemia B cells identify ROR1 as an oncofetal antigen and receptor for Wnt5a," *PNAS USA*, 105(8): 3047-3052 (2008).
Hofer et al., "Chimeric rabbit/human Fab and IgG specific for members of the Nogo-66 receptor family selected for species cross-reactivity with an improved phage display vector," *J. Immunol. Methods*, 318(1-2): 75-87 (2007).
Hudecek et al., "The B-cell tumor associated antigen ROR1 can be targeted with T-cells modified to express a ROR1-specific chimeric antigen receptor," *Blood*, pre-published online Aug. 11, 2010; DOI 10.1182/blood-2010-05-283309.
Klein et al., "Gene expression profiling of B cell chronic lymphocytic leukemia reveals a homogeneous phenotype related to memory B cells," *J. Exp. Med.*, 194: 1625-1638 (2001).
Kwong et al., "Generation, affinity maturation, and characterization of a human anti-human NKG2D monoclonal antibody with dual antagonistic and agonistic activity," *J. Mol. Biol.*, 384(5): 1143-1156 (2008).
Popkov et al., "Rabbit immune repertoires as sources for therapeutic monoclonal antibodies: the impact of kappa allotype-correlated variation in cysteine content on antibody libraries selected by phage display," *J. Mol. Biol.*, 325(2): 325-335 (2003).
Rader, "Generation and selection of rabbit antibody libraries by phage display," in *Therapeutic Antibodies: Methods and Protocols*, vol. 525, pp. 101-128, Humana (2009).
Rosenwald et al., "Relation of gene expression phenotype to immunoglobulin mutation genotype in B cell chronic lymphocytic leukemia," *J. Exp. Med.*, 194: 1639-1647 (2001).
Stahl et al., "Generation and characterization of a chimeric rabbit/human fab for co-crystallization of HIV-1 Rev," *J. Mol. Biol.*, 397(3): 697-708 (2010).
Uhrmacher et al., "Use of the receptor tyrosine kinase-like orphan receptor 1 (ROR1) as a diagnostic tool in chronic lymphocytic leukemia (CLL)," *Leukemia Research*, 35(10): 1360-1366 (2011).
Yang et al., "Therapeutic potential and challenges of targeting receptor tyrosine kinase ROR1 with monoclonal antibodies in B-cell malignancies," *PLoS One*, 6(6): e21018, pp. 1-15, published online Jun. 15, 2011.
Chan et al., "Enhanced Killing of Primary Ovarian Cancer by Retargeting Autologous Cytokine-Induced Killer Cells with Bispecific Antibodies: A Preclinical Study," *Clin Cancer Res*, 12(6): 1859-1867 (2006).
Chiron et al., "Furin-mediated Cleavage of *Pseudomonas* Exotoxin-derived Chimeric Toxins," *The Journal of Biological Chemistry*, 272(50): 31707-31711 (1997).
Lu et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," *Cancer Research*, 61: 7002-7008 (2001).
Sebastian, "Review of catumaxomab in the treatment of malignant ascites," *Cancer Management and Research*, 2010(2): 283-286 (Nov. 8, 2010).

* cited by examiner

*Primary Examiner* — Ruixiang Li
(74) *Attorney, Agent, or Firm* — Leydig, Voit & Mayer, Ltd.

(57) ABSTRACT

The invention relates to antibodies having specificity for human ROR1, compositions thereof, and methods for using such antibodies, including in the diagnosis and treatment of disorders associated with aberrant ROR1 expression.

23 Claims, 11 Drawing Sheets

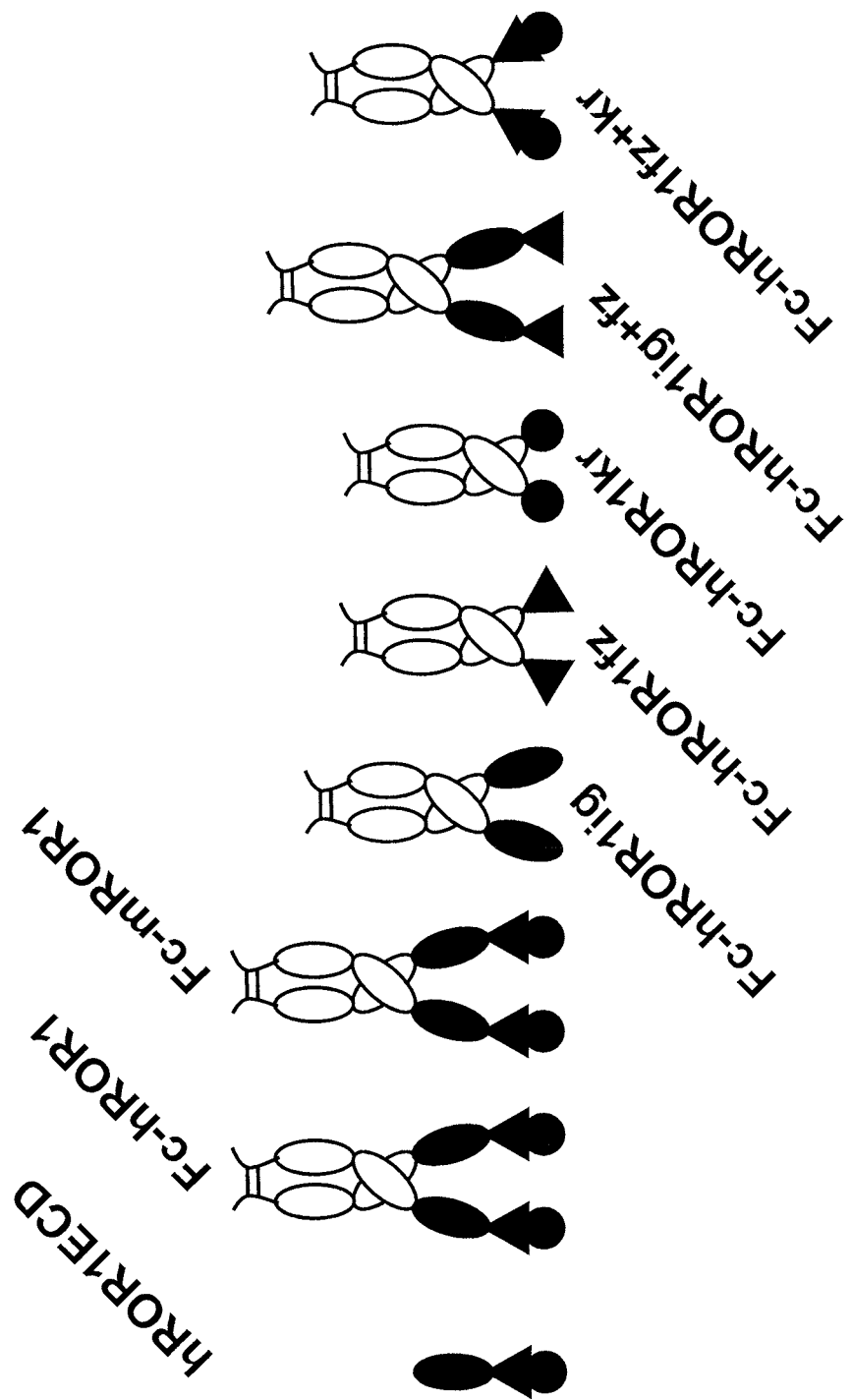

Fig. 2

$V_\kappa$

|  | FR1 | | CDR1 | FR2 | CDR2 | FR3 | CDR3 | FR4 | |
|---|---|---|---|---|---|---|---|---|---|
|  | 1 | 23 | | 35 | 49 | 57 | 88 | 98 107 | |
| R11 | ELVMTQTPSSTSGAWGTVTINC | | QASQSIDSNLA | WFQQKPGQPPTLLIY | RASNLAS | GVPSRFSGSRSGTEYLTISGVQREDAATYYC | LGGVGNVSYRTS | FGGGTEVVVK | SEQ ID NO:1 |
| Y31 | ELVMTQTPSSVSAAVGGTVTINC | | QASQSIGSYLA | WYQQKPGQPPKLLIY | YASNLAS | GVPSRFSGSGSGTEYLTISGVQREDAATYYC | LGSLSNSDNV— | FGGGTELEIL | SEQ ID NO:5 |

$V_\lambda$

|  | FR1 | | CDR1 | FR2 | CDR2 | FR3 | CDR3 | FR4 | |
|---|---|---|---|---|---|---|---|---|---|
|  | 1 | 23 | | 35 | 49 | 57 | 88 | 98 107 | |
| R12 | ELVLTQSPVSAALGSPAKITC | | TLSSAHRTDTID | WYQQLQGEAPRYLMQQSD | GSYTKRP | GVPDRFSGSSSGADRYLLIPSVQADDEADYYC | GADYIGGVV | FQGGTQLITVTG | SEQ ID NO:3 |

$V_H$

|  | FR1 | | CDR1 | FR2 | CDR2 | FR3 | CDR3 | FR4 | |
|---|---|---|---|---|---|---|---|---|---|
|  | 1 | 30 | | 36 | 49 | 66 | 94 | 103 113 | |
| R11 | -QSVKESEGDLVTPAGNLTLTCTASGSDIN | | DYPIS | WVRQAPGKGLEWIG | FIN-SGGSTWYASUVKG | RFTISRIST—TVDLKMTSLTTDDTATYFCAR | GYSTYWGD-FNI | WGPGTLVTISS | SEQ ID NO:2 |
| R12 | QEQLVESGGRLVTPGGSLILSCKASGFDFS | | AYYMS | WVRQAPGKGLEWIA | TIYPSSGKTYYATWVNG | RFTISSDNAQMTVDIQMNSLTAADRATYFCAR | DSYADDGALFNI | WGPGTLVTISS | SEQ ID NO:4 |
| Y31 | -QSLEESGGRLVTPGTPLTLTCTVSGIDIN | | SHWMS | WVRQAPGKGLEWIG | IIA-ASGSTYYANWAKG | RFTISKIST—TVDLRIASPTTEDTATYFCAR | DYGDYRLVTFNI | WGPGTLVVVSS | SEQ ID NO:6 |

US 9,758,586 B2

SEQUENCE LISTING

```
<160> NUMBER OF SEQ ID NOS: 53

<210> SEQ ID NO 1
<211> LENGTH: 110
<212> TYPE: PRT
<213> ORGANISM: Oryctolagus cuniculus

<400> SEQUENCE: 1

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
            20                  25                  30

Leu Ala Trp Phe Gln Gln Lys Pro Gly Gln Pro Pro Thr Leu Leu Ile
        35                  40                  45

Tyr Arg Ala Ser Asn Leu Ala Ser Gly Val Pro Ser Arg Phe Ser Gly
    50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Gly Thr Glu Val Val Val Lys
            100                 105                 110

<210> SEQ ID NO 2
<211> LENGTH: 116
<212> TYPE: PRT
<213> ORGANISM: Oryctolagus cuniculus

<400> SEQUENCE: 2

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Cys Asp Phe Asn Ile Trp Gly Pro Gly Thr Leu Val
            100                 105                 110

Thr Ile Ser Ser
            115
```

<210> SEQ ID NO 3
<211> LENGTH: 112
<212> TYPE: PRT
<213> ORGANISM: Oryctolagus cuniculus

<400> SEQUENCE: 3

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110

<210> SEQ ID NO 4
<211> LENGTH: 121
<212> TYPE: PRT
<213> ORGANISM: Oryctolagus cuniculus

<400> SEQUENCE: 4

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 5
<211> LENGTH: 108
<212> TYPE: PRT
<213> ORGANISM: Oryctolagus cuniculus

<400> SEQUENCE: 5

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Ile Gly Ser Tyr
            20                  25                  30

Leu Ala Trp Tyr Gln Gln Lys Pro Gly Gln Pro Pro Lys Leu Leu Ile
        35                  40                  45

Tyr Tyr Ala Ser Asn Leu Ala Ser Gly Val Pro Ser Arg Phe Ser Gly
    50                  55                  60

```
Ser Gly Ser Gly Thr Glu Tyr Thr Leu Thr Ile Ser Gly Val Gln Arg
 65                  70                  75                  80

Glu Asp Ala Ala Thr Tyr Tyr Cys Leu Gly Ser Leu Ser Asn Ser Asp
                 85                  90                  95

Asn Val Phe Gly Gly Gly Thr Glu Leu Glu Ile Leu
            100                 105
```

<210> SEQ ID NO 6
<211> LENGTH: 117
<212> TYPE: PRT
<213> ORGANISM: Oryctolagus cuniculus

<400> SEQUENCE: 6

```
Gln Ser Leu Glu Glu Ser Gly Gly Arg Leu Val Thr Pro Gly Thr Pro
  1               5                  10                  15

Leu Thr Leu Thr Cys Thr Val Ser Gly Ile Asp Leu Asn Ser His Trp
             20                  25                  30

Met Ser Trp Val Arg Gln Ala Pro Gly Lys Gly Leu Glu Trp Ile Gly
         35                  40                  45

Ile Ile Ala Ala Ser Gly Ser Thr Tyr Tyr Ala Asn Trp Ala Lys Gly
 50                  55                  60

Arg Phe Thr Ile Ser Lys Thr Ser Thr Thr Val Asp Leu Arg Ile Ala
 65                  70                  75                  80

Ser Pro Thr Thr Glu Asp Thr Ala Thr Tyr Phe Cys Ala Arg Asp Tyr
                 85                  90                  95

Gly Asp Tyr Arg Leu Val Thr Phe Asn Ile Trp Gly Pro Gly Thr Leu
            100                 105                 110

Val Thr Val Ser Ser
        115
```

<210> SEQ ID NO 7
<211> LENGTH: 23
<212> TYPE: PRT
<213> ORGANISM: Artificial Sequence
<220> FEATURE:
<223> OTHER INFORMATION: Synthetic

<400> SEQUENCE: 7

```
Glu Leu Val Met Thr Gln Thr Pro Ser Ser Thr Ser Gly Ala Val Gly
  1               5                  10                  15

Gly Thr Val Thr Ile Asn Cys
             20
```

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

```
Trp Phe Gln Gln Lys Pro Gly Gln Pro Pro Thr Leu Leu Ile Tyr
  1               5                  10                  15
```

<210> SEQ ID NO 9
<211> LENGTH: 32
<212> TYPE: PRT
<213> ORGANISM: Artificial Sequence
<220> FEATURE:
<223> OTHER INFORMATION: Synthetic

<400> SEQUENCE: 9

Gly Val Pro Ser Arg Phe Ser Gly Ser Arg Gly Thr Glu Tyr Thr
1               5                   10                  15

Leu Thr Ile Ser Gly Val Gln Arg Glu Asp Ala Ala Thr Tyr Tyr Cys
            20                  25                  30

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Phe Gly Gly Gly Thr Glu Val Val Val Lys
1               5                   10

<210> SEQ ID NO 11
<211> LENGTH: 22
<212> TYPE: PRT
<213> ORGANISM: Artificial Sequence
<220> FEATURE:
<223> OTHER INFORMATION: Synthetic

<400> SEQUENCE: 11

Glu Leu Val Leu Thr Gln Ser Pro Ser Val Ser Ala Ala Leu Gly Ser
1               5                   10                  15

Pro Ala Lys Ile Thr Cys
            20

<210> SEQ ID NO 12
<211> LENGTH: 19
<212> TYPE: PRT
<213> ORGANISM: Artificial Sequence
<220> FEATURE:
<223> OTHER INFORMATION: Synthetic

<400> SEQUENCE: 12

Trp Tyr Gln Gln Leu Gln Gly Glu Ala Pro Arg Tyr Leu Met Gln Val
1               5                   10                  15

Gln Ser Asp

<210> SEQ ID NO 13
<211> LENGTH: 32
<212> TYPE: PRT
<213> ORGANISM: Artificial Sequence
<220> FEATURE:
<223> OTHER INFORMATION: Synthetic

<400> SEQUENCE: 13

Gly Val Pro Asp Arg Phe Ser Gly Ser Ser Ser Gly Ala Asp Arg Tyr
1               5                   10                  15

Leu Ile Ile Pro Ser Val Gln Ala Asp Asp Glu Ala Asp Tyr Tyr Cys
            20                  25                  30

<210> SEQ ID NO 14
<211> LENGTH: 11
<212> TYPE: PRT
<213> ORGANISM: Artificial Sequence
<220> FEATURE:
<223> OTHER INFORMATION: Synthetic

```
<400> SEQUENCE: 14

Phe Gly Gly Gly Thr Gln Leu Thr Val Thr Gly
1               5                   10

<210> SEQ ID NO 15
<211> LENGTH: 23
<212> TYPE: PRT
<213> ORGANISM: Artificial Sequence
<220> FEATURE:
<223> OTHER INFORMATION: Synthetic

<400> SEQUENCE: 15

Glu Leu Val Met Thr Gln Thr Pro Ser Ser Val Ser Ala Ala Val Gly
1               5                   10                  15

Gly Thr Val Thr Ile Asn Cys
            20

<210> SEQ ID NO 16
<211> LENGTH: 15
<212> TYPE: PRT
<213> ORGANISM: Artificial Sequence
<220> FEATURE:
<223> OTHER INFORMATION: Synthetic

<400> SEQUENCE: 16

Trp Tyr Gln Gln Lys Pro Gly Gln Pro Pro Lys Leu Leu Ile Tyr
1               5                   10                  15

<210> SEQ ID NO 17
<211> LENGTH: 32
<212> TYPE: PRT
<213> ORGANISM: Artificial Sequence
<220> FEATURE:
<223> OTHER INFORMATION: Synthetic

<400> SEQUENCE: 17

Gly Val Pro Ser Arg Phe Ser Gly Ser Gly Ser Gly Thr Glu Tyr Thr
1               5                   10                  15

Leu Thr Ile Ser Gly Val Gln Arg Glu Asp Ala Ala Thr Tyr Tyr Cys
            20                  25                  30

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Phe Gly Gly Gly Thr Glu Leu Glu Ile Leu
1               5                   10

<210> SEQ ID NO 19
<211> LENGTH: 29
<212> TYPE: PRT
<213> ORGANISM: Artificial Sequence
<220> FEATURE:
<223> OTHER INFORMATION: Synthetic

<400> SEQUENCE: 19

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn
            20                  25
```

```
<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Trp Val Arg Gln Ala Pro Gly Lys Gly Leu Glu Trp Ile Gly
1               5                  10

<210> SEQ ID NO 21
<211> LENGTH: 30
<212> TYPE: PRT
<213> ORGANISM: Artificial Sequence
<220> FEATURE:
<223> OTHER INFORMATION: Synthetic

<400> SEQUENCE: 21

Arg Phe Thr Ile Ser Arg Thr Ser Thr Val Asp Leu Lys Met Thr
1               5                  10                  15

Ser Leu Thr Thr Asp Asp Thr Ala Thr Tyr Phe Cys Ala Arg
            20                  25                  30

<210> SEQ ID NO 22
<211> LENGTH: 11
<212> TYPE: PRT
<213> ORGANISM: Artificial Sequence
<220> FEATURE:
<223> OTHER INFORMATION: Synthetic

<400> SEQUENCE: 22

Trp Gly Pro Gly Thr Leu Val Thr Ile Ser Ser
1               5                  10

<210> SEQ ID NO 23
<211> LENGTH: 30
<212> TYPE: PRT
<213> ORGANISM: Artificial Sequence
<220> FEATURE:
<223> OTHER INFORMATION: Synthetic

<400> SEQUENCE: 23

Gln Glu Gln Leu Val Glu Ser Gly Gly Arg Leu Val Thr Pro Gly Gly
1               5                  10                  15

Ser Leu Thr Leu Ser Cys Lys Ala Ser Gly Phe Asp Phe Ser
            20                  25                  30

<210> SEQ ID NO 24
<211> LENGTH: 14
<212> TYPE: PRT
<213> ORGANISM: Artificial Sequence
<220> FEATURE:
<223> OTHER INFORMATION: Synthetic

<400> SEQUENCE: 24

Trp Val Arg Gln Ala Pro Gly Lys Gly Leu Glu Trp Ile Ala
1               5                  10

<210> SEQ ID NO 25
<211> LENGTH: 32
<212> TYPE: PRT
<213> ORGANISM: Artificial Sequence
<220> FEATURE:
<223> OTHER INFORMATION: Synthetic
```

```
<400> SEQUENCE: 25

Arg Phe Thr Ile Ser Ser Asp Asn Ala Gln Asn Thr Val Asp Leu Gln
1               5                   10                  15

Met Asn Ser Leu Thr Ala Ala Asp Arg Ala Thr Tyr Phe Cys Ala Arg
                20                  25                  30

<210> SEQ ID NO 26
<211> LENGTH: 11
<212> TYPE: PRT
<213> ORGANISM: Artificial Sequence
<220> FEATURE:
<223> OTHER INFORMATION: Synthetic

<400> SEQUENCE: 26

Trp Gly Pro Gly Thr Leu Val Thr Ile Ser Ser
1               5                   10

<210> SEQ ID NO 27
<211> LENGTH: 29
<212> TYPE: PRT
<213> ORGANISM: Artificial Sequence
<220> FEATURE:
<223> OTHER INFORMATION: Synthetic

<400> SEQUENCE: 27

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Asn
                20                  25

<210> SEQ ID NO 28
<211> LENGTH: 14
<212> TYPE: PRT
<213> ORGANISM: Artificial Sequence
<220> FEATURE:
<223> OTHER INFORMATION: Synthetic

<400> SEQUENCE: 28

Trp Val Arg Gln Ala Pro Gly Lys Gly Leu Glu Trp Ile Gly
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthetic

<400> SEQUENCE: 29

Arg Phe Thr Ile Ser Lys Thr Ser Thr Thr Val Asp Leu Arg Ile Ala
1               5                   10                  15

Ser Pro Thr Thr Glu Asp Thr Ala Thr Tyr Phe Cys Ala Arg
                20                  25                  30

<210> SEQ ID NO 30
<211> LENGTH: 11
<212> TYPE: PRT
<213> ORGANISM: Artificial Sequence
<220> FEATURE:
<223> OTHER INFORMATION: Synthetic

<400> SEQUENCE: 30

Trp Gly Pro Gly Thr Leu Val Thr Val Ser Ser
1               5                   10
```

```
<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Gln Ala Ser Gln Ser Ile Asp Ser Asn Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Synthetic

<400> SEQUENCE: 32

Arg Ala Ser Asn Leu Ala Ser
1               5

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Leu Gly Gly Val Gly Asn Val Ser Tyr Arg Thr Ser
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic

<400> SEQUENCE: 34

Thr Leu Ser Ser Ala His Lys Thr Asp Thr Ile Asp
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic

<400> SEQUENCE: 35

Gly Ser Tyr Thr Lys Arg Pro
1               5

<210> SEQ ID NO 36
<211> LENGTH: 9
<212> TYPE: PRT
<213> ORGANISM: Artificial Sequence
<220> FEATURE:
<223> OTHER INFORMATION: Synthetic

<400> SEQUENCE: 36

Gly Ala Asp Tyr Ile Gly Gly Tyr Val
1               5
```

<210> SEQ ID NO 37
<211> LENGTH: 11
<212> TYPE: PRT
<213> ORGANISM: Artificial Sequence
<220> FEATURE:
<223> OTHER INFORMATION: Synthetic

<400> SEQUENCE: 37

Gln Ala Ser Gln Ser Ile Gly Ser Tyr Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Tyr Ala Ser Asn Leu Ala Ser
1               5

<210> SEQ ID NO 39
<211> LENGTH: 10
<212> TYPE: PRT
<213> ORGANISM: Artificial Sequence
<220> FEATURE:
<223> OTHER INFORMATION: Synthetic

<400> SEQUENCE: 39

Leu Gly Ser Leu Ser Asn Ser Asp Asn Val
1               5                   10

<210> SEQ ID NO 40
<211> LENGTH: 5
<212> TYPE: PRT
<213> ORGANISM: Artificial Sequence
<220> FEATURE:
<223> OTHER INFORMATION: Synthetic

<400> SEQUENCE: 40

Asp Tyr Pro Ile Ser
1               5

<210> SEQ ID NO 41
<211> LENGTH: 16
<212> TYPE: PRT
<213> ORGANISM: Artificial Sequence
<220> FEATURE:
<223> OTHER INFORMATION: Synthetic

<400> SEQUENCE: 41

Phe Ile Asn Ser Gly Gly Ser Thr Trp Tyr Ala Ser Trp Val Lys Gly
1               5                   10                  15

<210> SEQ ID NO 42
<211> LENGTH: 11
<212> TYPE: PRT
<213> ORGANISM: Artificial Sequence
<220> FEATURE:
<223> OTHER INFORMATION: Synthetic

<400> SEQUENCE: 42

Gly Tyr Ser Thr Tyr Tyr Cys Asp Phe Asn Ile
1               5                   10

```
<210> SEQ ID NO 43
<211> LENGTH: 5
<212> TYPE: PRT
<213> ORGANISM: Artificial Sequence
<220> FEATURE:
<223> OTHER INFORMATION: Synthetic

<400> SEQUENCE: 43

Ala Tyr Tyr Met Ser
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Thr Ile Tyr Pro Ser Ser Gly Lys Thr Tyr Tyr Ala Thr Trp Val Asn
1               5                   10                  15
Gly

<210> SEQ ID NO 45
<211> LENGTH: 12
<212> TYPE: PRT
<213> ORGANISM: Artificial Sequence
<220> FEATURE:
<223> OTHER INFORMATION: Synthetic

<400> SEQUENCE: 45

Asp Ser Tyr Ala Asp Asp Gly Ala Leu Phe Asn Ile
1               5                   10

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Ser His Trp Met Ser
1               5

<210> SEQ ID NO 47
<211> LENGTH: 16
<212> TYPE: PRT
<213> ORGANISM: Artificial Sequence
<220> FEATURE:
<223> OTHER INFORMATION: Synthetic

<400> SEQUENCE: 47

Ile Ile Ala Ala Ser Gly Ser Thr Tyr Tyr Ala Asn Trp Ala Lys Gly
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: Synthetic

<400> SEQUENCE: 48

Asp Tyr Gly Asp Tyr Arg Leu Val Thr Phe Asn Ile
1               5                   10
```

```
<210> SEQ ID NO 49
<211> LENGTH: 37
<212> TYPE: DNA
<213> ORGANISM: Artificial Sequence
<220> FEATURE:
<223> OTHER INFORMATION: Synthetic

<400> SEQUENCE: 49
gaggaggagc tcactcccag tcggtgaagg agtccga                                37

<210> SEQ ID NO 50
<211> LENGTH: 59
<212> TYPE: DNA
<213> ORGANISM: Artificial Sequence
<220> FEATURE:
<223> OTHER INFORMATION: Synthetic

<400> SEQUENCE: 50
ccgatgggcc cttggtggag gctgaggaga tggtgaccag ggtgcctggt ccccagatg        59

<210> SEQ ID NO 51
<211> LENGTH: 60
<212> TYPE: DNA
<213> ORGANISM: Artificial Sequence
<220> FEATURE:
<223> OTHER INFORMATION: Synthetic

<400> SEQUENCE: 51
gaggagaagc ttgttgctct ggatctctgg tgcctacggg gaactcgtgc tgactcagtc       60

<210> SEQ ID NO 52
<211> LENGTH: 36
<212> TYPE: DNA
<213> ORGANISM: Artificial Sequence
<220> FEATURE:
<223> OTHER INFORMATION: Synthetic

<400> SEQUENCE: 52
attggatgca taatagatca gtagcttggg aggctg                                 36

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
aaccagggca gcctcccaag ctactgatct                                        30
```

CHIMERIC RABBIT/HUMAN ROR1 ANTIBODIES

CROSS-REFERENCE TO RELATED APPLICATIONS

This patent application is the U.S. National Phase of International Patent Application No. PCT/US2011/062670, filed Nov. 30, 2011, which claims the benefit of U.S. Provisional Patent Application No. 61/418,550, filed Dec. 1, 2010, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 17,782 Byte ASCII (Text) file named "713419ST25.TXT," created on May 1, 2013.

BACKGROUND OF THE INVENTION

Antibody therapies and diagnostics have been developed for use in treating a wide range of conditions including autoimmune diseases or disorders, infectious diseases, and cancers. Such therapies are useful but also can be associated with undesirable immunogenicity and can damage healthy cells and tissues.

B-cell chronic lymphocytic leukemia (B-CLL) and mantle cell lymphoma (MCL) are two incurable B-cell malignancies with a combined incidence of new cases that exceeds 18,000 patients per year in the United States alone. Antibody therapies have been developed for B cell malignancies, which include rituximab, a chimeric mouse/human monoclonal antibody (mAb), alemtuzumab, a humanized mAb, and ofatumumab, a human mAb. However, the target antigens for all three of these drugs (CD20, CD52, and CD20 respectively) are expressed not only in malignant B cells but also in normal B cells, and CD52 is ubiquitously expressed on a variety of normal cells of the immune system. Therefore, immunosuppression can be a concern with these antibody therapies. Currently in the United States and Europe, there is no commercial therapeutic antibody that specifically recognizes an antigen present on malignant B cells, but not on normal B cells.

There is a desire for additional therapeutic and diagnostic antibodies having good efficacy and that exhibit minimal binding and/or damage to non-diseased cells.

BRIEF SUMMARY OF THE INVENTION

The invention provides an isolated antibody with specificity for the extracellular domain of receptor tyrosine kinase-like orphan receptor 1 (ROR 1), which is selectively expressed on the surface of malignant cells, including B-cell tumors and other cancers.

In particular, the invention provides an isolated antibody having specificity for human ROR1 and having (a) a light chain with at least 90% identity to a sequence selected from the group consisting of SEQ ID NO: 1, SEQ ID NO: 3, and SEQ ID NO: 5, (b) a heavy chain with at least 90% identity to a sequence selected from the group consisting of SEQ ID NO: 2, SEQ ID NO: 4, and SEQ ID NO: 6, or (c) both a light chain of (a) and a heavy chain of (b).

The invention additionally provides an isolated antibody having specificity for human ROR1 and having (a) a light chain with at least 90% identity to the sequence of SEQ ID NO: 1, (b) a heavy chain with at least 90% identity to the sequence of SEQ ID NO: 2; or (c) both a light chain of (a) and a heavy chain of (b).

The invention additionally provides an isolated antibody having specificity for human ROR1 and having (a) a light chain with at least 90% identity to the sequence of SEQ ID NO: 3, (b) a heavy chain with at least 90% identity to the sequence of SEQ ID NO: 4; or (c) both a light chain of (a) and a heavy chain of (b).

The invention further provides an isolated antibody having specificity for human ROR1 and having (a) a light chain with at least 90% identity to the sequence of SEQ ID NO: 5, (b) a heavy chain with at least 90% identity to the sequence of SEQ ID NO: 6; or (c) both a light chain of (a) and a heavy chain of (b).

The invention also provides an isolated antibody having specificity for human ROR1 and having at least one CDR that includes a sequence selected from the group consisting of SEQ ID NOs: 31-48. In other embodiments, the isolated antibody can include one or more variants of the foregoing CDRs with 1, 2, or 3 amino acid substitutions, insertions, or deletions.

The invention further provides a pharmaceutical composition comprising an antibody of the invention and a pharmaceutically acceptable carrier.

In addition, the invention provides a method of killing or inhibiting the growth of cells expressing ROR1 in a subject, as well as a method of treating a disease or condition associated with elevated expression of ROR1 (e.g., a B-cell malignancy, renal cell carcinoma, colon cancer, or breast cancer), by administering a therapeutically effective amount of an isolated antibody of the invention or a pharmaceutical composition thereof to a subject in need thereof, thereby killing or inhibiting the growth of cells expressing ROR1 in the subject, or treating the disease or condition associated with elevated expression of ROR1 in the subject.

The antibodies and compositions of the invention also can be used in diagnostic methods to detect altered levels of ROR1, e.g., in a sample or in a subject, or ROR1-expressing tumors in a subject.

BRIEF DESCRIPTION OF THE DRAWING(S)

FIG. 1 is a schematic depiction of eight recombinant Fc fusion proteins having different compositions of the Immunoglobulin- (Ig-), Frizzled-, and Kringle-like extracellular domains of ROR1. Ig domains are depicted as ovals (in black), Frizzled domains are depicted as triangles (in black), and Kringle domains are depicted as circles (in black).

FIG. 2 is a list of the amino acid sequences corresponding to the R11, R12, and Y31 variable region light chains ($V_\kappa$ and $V_\lambda$) (SEQ ID NOs: 1, 3, and 5) and heavy chains ($V_H$) (SEQ ID NOs: 2, 4, and 6), which identify light chain framework regions FR1-FR4 (SEQ ID NOs: 7-10, 11-14, and 15-18), light chain complementarity determining regions CDR1-CDR3 (SEQ ID NOs: 31-33, 34-36, and 37-39), heavy chain framework regions FR1-FR4 (SEQ ID NOs: 19-22, 23-26, and 27-30), and heavy chain CDR1-CDR3 (SEQ ID NOs: 40-42, 43-45, and 46-48).

FIG. 3A is a graph that depicts the results of ELISA studies, providing absorbance data for binding of chimeric rabbit/human IgG1 R11, R12, and Y31, and negative control P14, against immobilized human ROR1 (Fc-hROR1), mouse ROR1 (Fc-mROR1), and human ROR2 (hROR2-Fc).

Columns indicate mean values, and error bars indicate standard deviation values of triplicates.

FIG. 3B is a graph that depicts the results of ELISA studies mapping the epitopes of IgG1 R11, R12, and Y31, and negative control P14 with five immobilized Fc fusion proteins that consisted of only one or two extracellular domains of human ROR1: Fc-hROR1ig (ig), Fc-hROR1fz (fz), Fc-hROR1kr (kr), Fc-hROR1ig+fz (ig+fz), and Fc-hROR1fz+kr (fz+kr). Columns indicate mean values, and error bars indicate standard deviation values of triplicates.

FIG. 4 is a series of graphs that depict the results of surface plasmon resonance binding analyses obtained for the binding of IgG1 R11, R12, and Y31 to immobilized Fc-hROR1. Response unit (y axis) increases that exceeded the values found for IgG1 R11, R12, and Y31 alone indicated independent epitopes that allow simultaneous binding. The x axis depicts the time in seconds (s).

FIG. 5A is a series of graphs that depict the results of surface plasmon resonance binding analysis obtained for the binding of Fab and IgG1 R11, R12, and Y31 to immobilized Fc-hROR1 after instantaneous background depletion. The mAbs were tested at five or six different concentrations ranging from 1.5 to 100 nM. Each concentration was tested in duplicate.

FIG. 5B is a series of graphs that depict the results of surface plasmon resonance binding analysis obtained for the binding of Fab and IgG1 R11 and Y31 to immobilized Fc-mROR1 after instantaneous background depletion. The mAbs were tested at five or six different concentrations ranging from 1.5 to 100 nM. Each concentration was tested in duplicate.

FIG. 6A is a graph that depicts flow cytometry analysis of the binding of IgG1 R11 (5 µg/ml), R12 (1 µg/ml), and Y31 (5 µg/ml) to the surface of JeKo-1 cells. The gray shade indicates the background observed with human anti-tetanus toxoid mAb TT11 in IgG1 format (TT11) (5 µg/ml). Biotinylated IgG1 was detected with PE-streptavidin. They axis depicts the number of events, and the x axis depicts the fluorescence intensity.

FIG. 6B is a graph that depicts flow cytometry analysis of the binding of IgG1 R11 (5 µg/mL), R12 (1 µg/mL), and Y31 (5 µg/mL) to the surface of HBL-2 cells. The gray shade indicates the background observed with IgG1 TT11 (5 µg/mL). Biotinylated IgG1 was detected with PE-streptavidin. The y axis depicts the number of events, and the x axis depicts the fluorescence intensity.

FIG. 6C is a series of graphs that depict the results of flow cytometry analysis of the binding of IgG1 R11 (5 µg/ml), R12 (1 µg/ml), and Y31 (5 µg/ml) to the surface of peripheral blood mononuclear cells (PBMC) from chronic lymphocytic leukemia (CLL) patients for CD19+CD5+ cells and CD19−CD5+ cells. The gray shade indicates the background observed with negative control chimeric rabbit/human IgG1 P14 (5 µg/ml). Biotinylated IgG1 in combination with FITC-CD19/APC-CD5 was detected with phycoerythrin-streptavidin (PE-streptavidin). They axis depicts the number of events, and the x axis depicts the fluorescence intensity.

FIG. 7A is a series of graphs that depict the results of flow cytometry analysis of the binding of IgG1 R12 (5 µg/ml), R12 (1 µg/ml), and Y31 (5 µg/ml) to the surface of PBMC from a CLL patient designated CLL-2 to identify PBMC subpopulations of NK cells (CD16+ CD3−), T cells (CD16−CD3+, CD19−CD5+), and CLL cells (CD19+CD5+). The x and y axis in the top and middle rows depict fluorescence intensity. In the bottom row, the gray shade indicates the background observed with negative control PE-streptavidin alone. The y axis depicts the number of events, and the x axis depicts the fluorescence intensity.

FIG. 7B is a is a series of graphs that depict the results of flow cytometry analysis of the binding of IgG1 R12 (5 µg/ml), R12 (1 µg/ml), and Y31 (5 µg/ml) to the surface of PBMC from a CLL patient designated CLL-3 to identify PBMC subpopulations of NK cells (CD16+ CD3−), T cells (CD16−CD3+, CD19−CD5+), and CLL cells (CD19+CD5+). The x and y axis in the top and middle rows depict fluorescence intensity. In the bottom row, the gray shade indicates the background observed with negative control PE-streptavidin alone. They axis depicts the number of events, and the x axis depicts the fluorescence intensity.

FIG. 7C is a is a series of graphs that depict the results of flow cytometry analysis of the binding of IgG1 R12 (5 µg/ml), R12 (1 µg/ml), and Y31 (5 µg/ml) to the surface of PBMC from a CLL patient designated CLL-4 to identify PBMC subpopulations of NK cells (CD16+ CD3−), T cells (CD16−CD3+, CD19−CD5+), and CLL cells (CD19+CD5+). The x and y axis in the top and middle rows depict fluorescence intensity. In the bottom row, the gray shade indicates the background observed with negative control PE-streptavidin alone. They axis depicts the number of events, and the x axis depicts the fluorescence intensity.

FIG. 7D is a is a series of graphs that depict the results of flow cytometry analysis of the binding of IgG1 R12 (5 µg/ml), R12 (1 µg/ml), and Y31 (5 µg/ml) to the surface of PBMC from a CLL patient designated CLL-5 to identify PBMC subpopulations of NK cells (CD16+ CD3−), T cells (CD16−CD3+, CD19−CD5+), and CLL cells (CD19+CD5+). The x and y axis in the top and middle rows depict fluorescence intensity. In the bottom row, the gray shade indicates the background observed with negative control PE-streptavidin alone. The y axis depicts the number of events, and the x axis depicts the fluorescence intensity.

Figure 9:
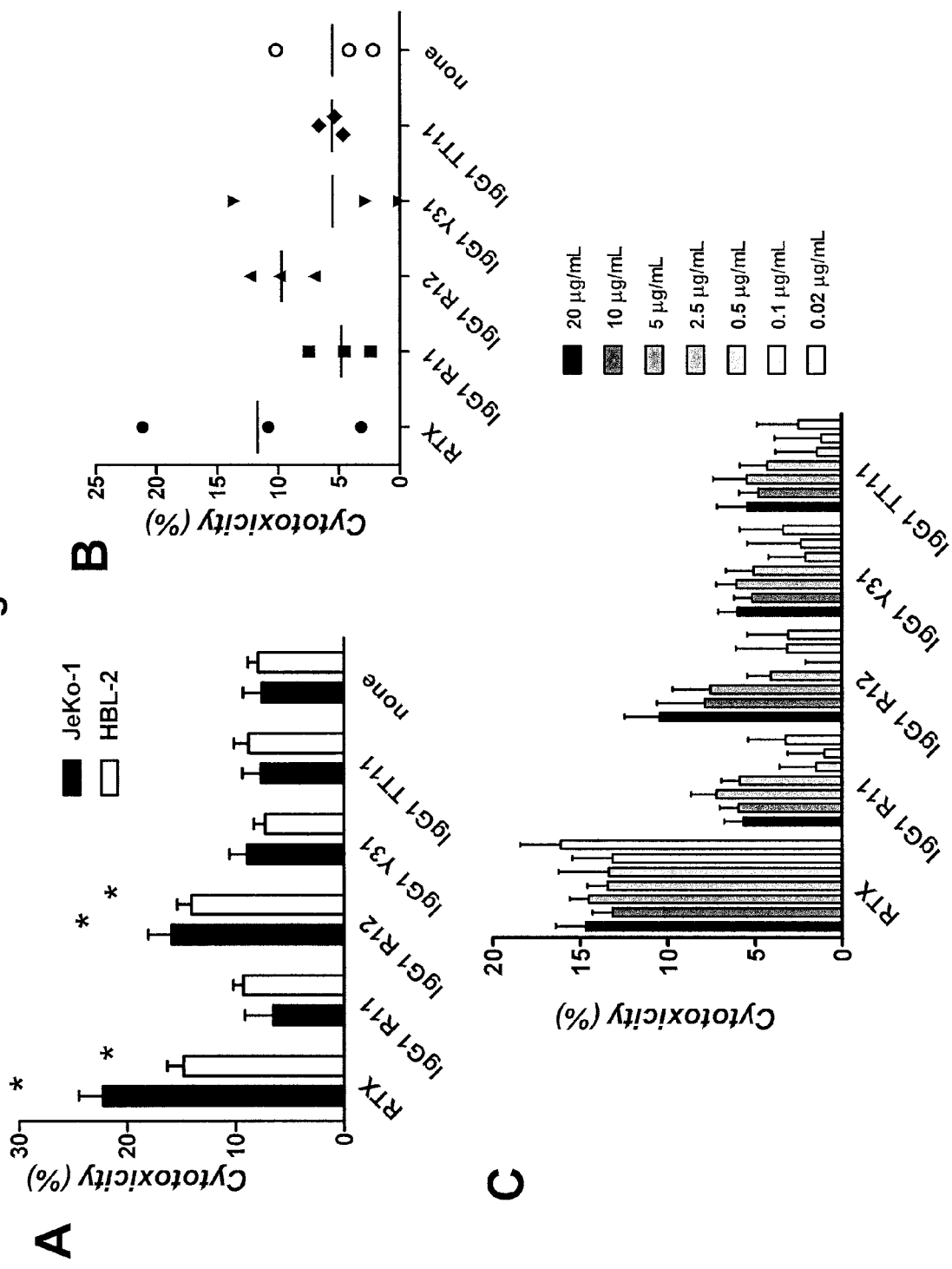

FIG. 9A is a graph depicting results of a bioluminescent intracellular protease detection assay quantifying the ADCC potency of IgG1 R11, R12, and Y31 in comparison to human anti-tetanus toxoid mAb TT11 in IgG1 format (negative control) and rituximab (RTX; positive control) toward JeKo-1 cells and HBL-2 cells at a concentration of 5 µg/ml. Columns indicate mean values, and error bars indicate standard deviation values of triplicates.

FIG. 9B is a graph depicting results of a cytotoxicity assay against PBMC from three CLL patients, with mean values indicated by horizontal bars.

FIG. 9C is a graph depicting results of a bioluminescent intracellular protease detection assay quantifying the antigen-dependent cellular cytotoxicity (ADCC) potency of IgG1 R11, R12, and Y31 in comparison to human anti-tetanus toxoid mAb TT11 in IgG1 format (negative control) and rituximab (RTX) toward HBL-2 cells at concentrations of 20 µg/ml, 10 µg/ml, 5 µg/ml, 2.5 µg/ml, 0.5 µg/ml, 0.1 µg/ml, and 0.02 µg/ml, with each concentration presented from left (black bars) to right (white bars), respectively. Columns indicate mean values, and error bars indicate standard deviation values of triplicates.

Figure 10:
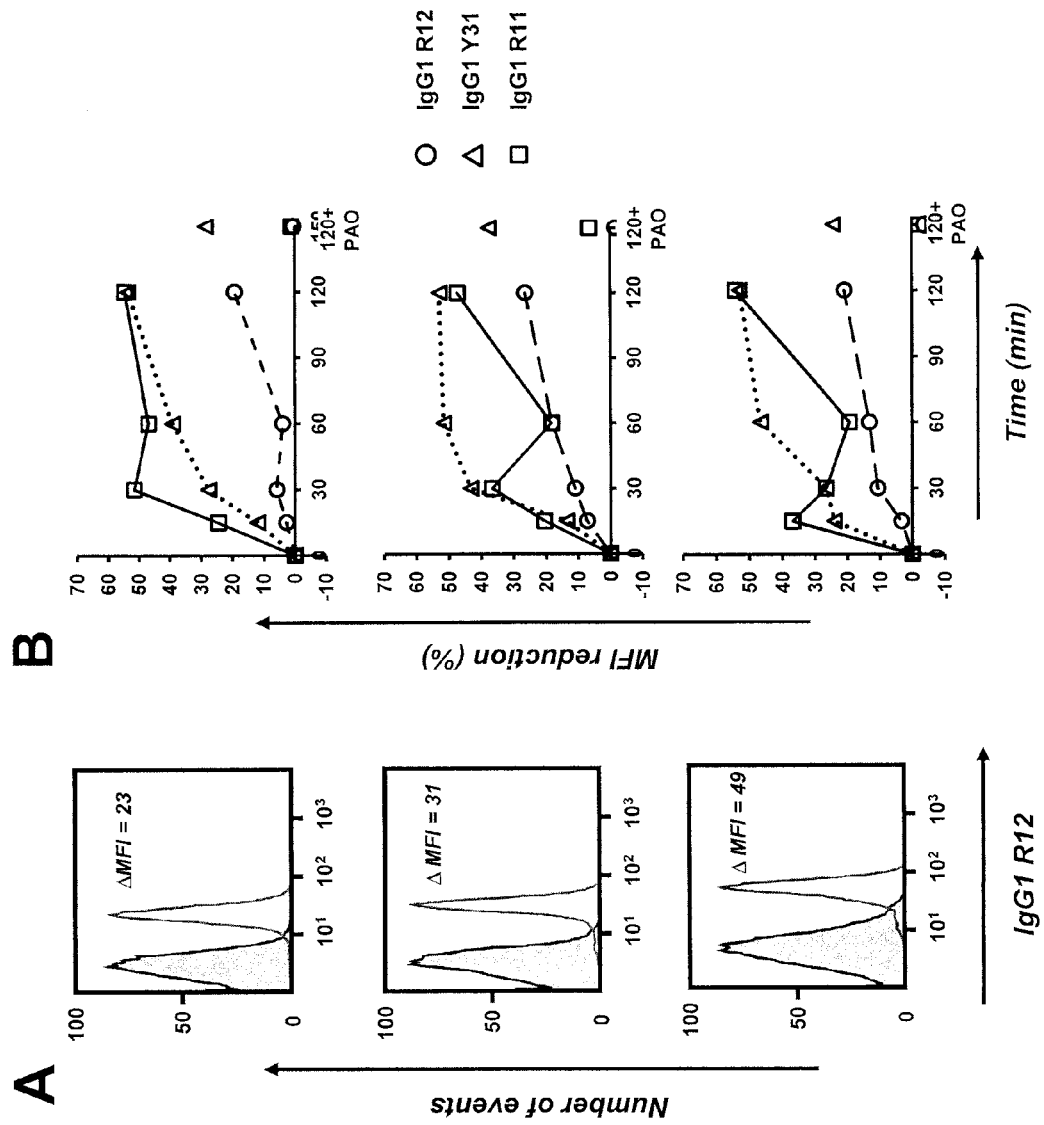

FIG. 10A is a series of graphs that depict the results of flow cytometry analysis of human ROR1 cell surface densities on primary CLL cells using biotinylated IgG1 R12 followed by PE-streptavidin. The gray shade indicates the background observed with negative control PE-streptavidin alone. They axis depicts the number of events, the x axis depicts the fluorescence intensity. Mean fluorescence intensity (MFI) values are indicated.

FIG. 10B is a series of graphs that depict MFI reduction over time of primary CLL cells reflecting the internalization of IgG1 R11, R12, and Y31 into the cells in the absence or presence of endocytosis inhibitor phenylarsine oxide (PAO).

Figure 11:
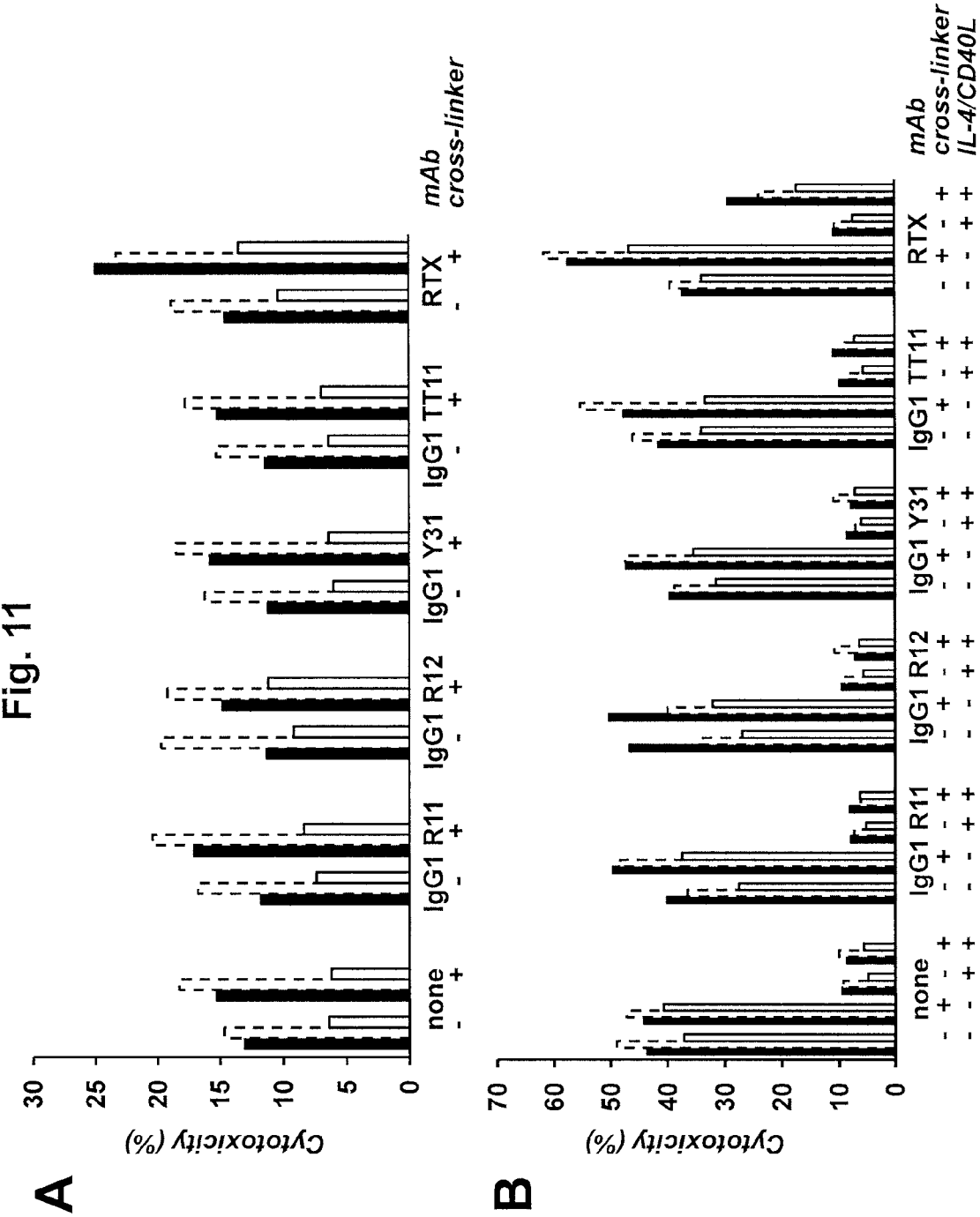

FIG. 11A is a graph depicting apoptosis in PBMC from three untreated CLL patients (CLL-2 (black bar), CLL-3 (dashed gray bar), and CLL-4 (white bar)) cultured in the absence of fetal bovine serum (FBS) and incubated with IgG1 R11, R12, Y31, or TT11, as compared to positive control rituximab (RTX) and negative control, and further in the presence (+) and absence (−) of F(ab')$_2$ goat-anti-human IgG (cross linker).

FIG. 11B is a graph depicting apoptosis in PBMC from three untreated CLL patients (CLL-2 (black bar), CLL-3 (dashed gray bar), and CLL-4 (white bar)) cultured in the presence of FBS and incubated with IgG1 R11, R12, Y31, or TT11, as compared to positive control rituximab (RTX) and negative control, and further in the presence (+) and absence (−) of F(ab')$_2$ goat-anti-human IgG (cross linker), as well as in the presence (+) and absence (−) of IL-4 and CD40L.

DETAILED DESCRIPTION OF THE INVENTION

Receptor tyrosine kinase-like orphan receptor 1 (ROR1) is a conserved embryonic protein whose expression becomes progressively reduced during embryonic development in mammals. The intact protein, including its extracellular domain, does not appear to be significantly expressed in normal, adult mammalian tissues. In particular, studies have not identified significant expression of ROR1 on the cell surface of normal adult human tissues, including normal B cells. Baskar et al., *Clin. Cancer Res.,* 14: 396-404 (2008), DaneshManesh et al., *Int. J. Cancer,* 123: 1190-1195 (2008), and Fukuda et al., *Proc. Nat'l. Acad. Sci. USA,* 105: 3047-3052 (2008). However, ROR1 is expressed on the cell surface of malignant B-cells, including B-cell chronic lymphocytic leukemia (B-CLL) and mantle cell lymphoma (MCL). It has also been reported that ROR1 is expressed in certain other cancer cell lines including Burkitt lymphoma, renal cell carcinoma, colon cancer, and breast cancer. See U.S. Patent Application Publication 2007/0207510. Therefore, ROR1 can be considered a selective marker for these cancers. The invention provides an antibody to this selective marker.

The invention provides an antibody having specificity for ROR1, comprising (a) a light chain having at least 90% identity to SEQ ID NO: 1, SEQ ID NO: 3, or SEQ ID NO: 5; (b) a heavy chain variable domain having at least 90% sequence identity to SEQ ID NO: 2, SEQ ID NO: 4, or SEQ ID NO: 6; or (c) both a light chain of (a) and a heavy chain of (b). In a preferred embodiment, the antibody comprises both a light chain of (a) and a heavy chain of (b).

In one embodiment, the invention provides an antibody having specificity for ROR1, comprising (a) a light chain having at least 90% identity to SEQ ID NO: 1; (b) a heavy chain variable domain having at least 90% sequence identity to SEQ ID NO: 2; or (c) both a light chain of (a) and a heavy chain of (b). In a preferred embodiment, the antibody comprises both a light chain of (a) and a heavy chain of (b).

In another embodiment, the invention provides an antibody having specificity for ROR1, comprising (a) a light chain having at least 90% identity to SEQ ID NO: 3; (b) a heavy chain variable domain having at least 90% sequence identity to SEQ ID NO: 4; or (c) both a light chain of (a) and a heavy chain of (b). In a preferred embodiment, the antibody comprises both a light chain of (a) and a heavy chain of (b).

In a further embodiment, the invention provides an antibody having specificity for ROR1, comprising (a) a light chain having at least 90% identity to SEQ ID NO: 5; (b) a heavy chain variable domain having at least 90% sequence identity to SEQ ID NO: 6; or (c) both a light chain of (a) and a heavy chain of (b). In a preferred embodiment, the antibody comprises both a light chain of (a) and a heavy chain of (b).

The antibody can be an isolated antibody having specificity for human ROR1, wherein the antibody comprises a light chain having at least 90% identity to SEQ ID NO: 1, SEQ ID NO: 3, or SEQ ID NO: 5. In other embodiments, the percentage identity can be at least 91%, at least 92%, at least 93%, at least 94%, at least 95%, at least 96%, at least 97%, at least 98%, or at least 99%, or even 100%. In preferred embodiments, the light chain has at least 95% identity to SEQ ID NO: 1, SEQ ID NO: 3, or SEQ ID NO: 5. In more preferred embodiments, the light chain has 100% identity to SEQ ID NO: 1, SEQ ID NO: 3, or SEQ ID NO: 5.

The antibody can be an isolated antibody having specificity for human ROR1, wherein the antibody comprises a heavy chain having at least 90% identity to SEQ ID NO: 2, SEQ ID NO: 4, or SEQ ID NO: 6. In other embodiments, the percentage identity can be at least 91%, at least 92%, at least 93%, at least 94%, at least 95%, at least 96%, at least 97%, at least 98%, or at least 99%, or even 100%. In preferred embodiments, the heavy chain has at least 95% identity to SEQ ID NO: 2, SEQ ID NO: 4, or SEQ ID NO: 6. In more preferred embodiments, the heavy chain has 100% identity to SEQ ID NO: 2, SEQ ID NO: 4, or SEQ ID NO: 6.

In some embodiments, the antibody can comprise any heavy chain as described above, in combination with any suitable light chain, such as those described above. Likewise, the antibody can comprise any of the light chains as described above in combination with any suitable heavy chain, such as those described above. For example, in preferred embodiments, the antibody comprises a light chain having at least 90% identity to SEQ ID NO: 1 and a heavy chain having at least 90% identity to SEQ ID NO: 2, or a light chain having at least 90% identity to SEQ ID NO: 3 and a heavy chain having at least 90% identity to SEQ ID NO: 4, or a light chain having at least 90% identity to SEQ ID NO: 5 and a heavy chain having at least 90% identity to SEQ ID NO: 6. In a preferred embodiment, the antibody comprises the light chain of SEQ ID NO: 1 and the heavy chain of SEQ ID NO: 2, the light chain of SEQ ID NO: 3 and the heavy chain of SEQ ID NO: 4, or the light chain of SEQ ID NO: 5 and the heavy chain of SEQ ID NO: 6.

Percent (%) identity of peptide sequences can be calculated, for example, as 100×[(identical positions)/min(TG$_A$, TG$_B$)], where TG$_A$ and TG$_B$ are the sum of the number of residues and internal gap positions in peptide sequences A and B in the alignment that minimizes TG$_A$ and TG$_B$. See, e.g., Russell et al., *J. Mol. Biol.*, 244: 332-350 (1994).

The antibody of the invention can be any antibody including a full length antibody or an antibody fragment having specificity for the extracellular domain of human ROR1. For example, the antibody can be polyclonal, monoclonal, recombinant, chimeric, or humanized. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment having specificity for the extracellular domain of human ROR1, such as F(ab)$_2$, Fv, scFv, IgG$\Delta$CH$_2$, F(ab')2, scFv2CH$_3$, Fab, VL, VH, scFv4, scFv3, scFv2, dsFv, Fv, scFv-Fc, (scFv)2, a diabody, and a bivalent antibody. The antibody can be any modified or synthetic antibody, including, but not limited to, non-depleting IgG antibodies, T-bodies, or other Fc or Fab variants of antibodies.

In addition to a heavy chain as described above, the antibody of the invention can further comprise a light chain selected from a Fab library using sequential naive chain shuffling. Likewise, in addition to a light chain as described above, the antibody of the invention can further comprise a heavy chain selected from a Fab library using sequential naive chain shuffling.

In some embodiments, the invention provides an isolated antibody, having specificity for human ROR1, comprising at least one CDR having a sequence selected from the group consisting of SEQ ID NOs: 31-48. The invention also provides an isolated antibody with specificity for ROR1 comprising at least one or more variants of the foregoing CDR sequences, which include 1, 2, or 3 substitutions, insertions, deletions, or combinations thereof in a sequence selected from the group consisting of SEQ ID NOs: 31-48. For example, a recombinant chimeric or humanized antibody (or fragment thereof) can include one, two, three, four, five, or six of the foregoing CDR sequences. In preferred embodiments, however, the recombinant chimeric or humanized antibody (or fragment thereof) includes three CDR sequences of the same light or heavy chain, e.g., SEQ ID NOs: 31-33, SEQ ID NOs: 34-36; SEQ ID NOs: 37-39; SEQ ID NOs: 40-42; SEQ ID NOs: 43-45; or SEQ ID NOs: 46-48. In more preferred embodiments, the recombinant chimeric or humanized antibody (or fragment thereof) includes six CDR sequences of the same antibody, e.g., (a) SEQ ID NOs: 31-33 and SEQ ID NOs: 40-42; (b) SEQ ID NOs: 34-36 and SEQ ID NOs: 43-45; or (c) SEQ ID NOs: 37-39 and SEQ ID NOs: 46-48.

In some embodiments, the invention provides an antibody with avidity for ROR1 of about 10 µM or less, 5 µM or less, 2 µM or less, 1 nM or less, 500 nM or less, 400 nM or less, 300 nM or less, or 200 nM or less. The invention also provides an antibody with avidity for ROR1 of about 100 nM or less, about 75 nM or less, about 50 nM or less, about 25 nM or less, about 10 nM or less, or about 5 nM or less. The invention further provides an antibody with avidity for ROR1 of about 1 nM or less, about 800 pM or less, about 700 pM or less, about 600 pM or less, about 500 pM or less, about 400 pM or less, about 300 pM or less, about 200 pM or less, or about 100 pM or less. Avidity can be measured using art-known techniques, such as ELISA or surface plasmon resonance.

The antibody of the invention can be produced by any suitable technique, for example, using any suitable eukaryotic or non-eukaryotic expression system. In certain embodiments, the antibody is produced using a mammalian expression system.

The antibody of the invention can be produced using a suitable non-eukaryotic expression system such as a bacterial expression system. Bacterial expression systems can be used to produce fragments such as a F(ab)2, Fv, scFv, IgG$\Delta$CH$_2$, F(ab')2, scFv2CH$_3$, Fab, VL, VH, scFv4, scFv3, scFv2, dsFv, Fv, scFv-Fc, (scFv)2, and diabodies. Techniques for altering DNA coding sequences to produce such fragments are known in the art.

The antibody of the invention can be conjugated to a synthetic molecule using any type of suitable conjugation. Recombinant engineering and incorporated selenocysteine (e.g., as described in International Patent Application Publication WO/2008/122039) can be used to conjugate a synthetic molecule. Other methods of conjugation can include covalent coupling to native or engineered lysine side-chain amines or cysteine side-chain thiols. See, e.g., Wu et al., *Nat. Biotechnol.*, 23: 1137-1146 (2005). The synthetic molecule can be any molecule such as one targeting a tumor. Of course, it will be understood that the synthetic molecule also can be a protein (e.g., an antibody) or an RNA or DNA aptamer.

Synthetic molecules include therapeutic agents such as cytotoxic, cytostatic, or antiangiogenic agents, radioisotopes, and liposomes. A cytotoxic agent can be a plant, fungal, or bacterial molecule (e.g., a protein toxin). A therapeutic agent can be a maytansinoid (e.g., maytansinol or DM1 maytansinoid), a taxane, a calicheamicin, a cemadotin, or a monomethylauristatin (e.g., monomethylauristatin E or monomethylauristatin F). Therapeutic agents include vincristine and prednisone. A therapeutic agent can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, daunomycin, epirubicin, idarubicin, mitomycin-C, dactinomycin, or mithramycin); a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an antimitotic agent (e.g., a vinca alkaloid such as vincristine, or a taxoid such as paclitaxel or docetaxel); a topoisomerase inhibitor (for example, etoposide, teniposide, amsacrine, topotecan); a cell cycle inhibitor (for example, a flavopyridol); or a microbtubule agent (e.g., an epothilone, discodenolide analog, or eleutherobin analog). A therapeutic agent can be a proteosome inhibitor or a topoisomerase inhibitor such as bortezomib, amsacrine, etoposide, etoposide phosphate, teniposide, or doxorubicin. Therapeutic radioisotopes include iodine ($^{131}$I), yttrium ($^{90}$Y), lutetium ($^{177}$Lu), actinium ($^{225}$Ac), praseodymium, astatine ($^{211}$At), rhenium ($^{186}$Re), bismuth ($^{212}$Bi or $^{213}$Bi), and rhodium ($^{188}$Rh). Antiangiogenic agents include linomide, bevacuzimab, angiostatin, and razoxane. The synthetic molecule can be another antibody such as rituximab or bevacuzimab.

A synthetic molecule can also be a label. Labels can be useful in diagnostic applications and can include, for example, contrast agents. A contrast agent can be a radioisotope label such as iodine ($^{131}$I or $^{125}$I), indium ($^{111}$In), technetium ($^{99}$Tc), phosphorus ($^{32}$P), carbon ($^{14}$C), tritium (³H), other radioisotope (e.g., a radioactive ion), or a therapeutic radioisotope such as one of the therapeutic radioisotopes listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

In yet other embodiments, the synthetic molecule can be a liposome, as described in Bendas, *BioDrugs*, 15(4): 215-224 (2001). In such embodiments, the antibody can be conjugated to a colloidal particle, e.g., a liposome, and used for controlled delivery of an agent to diseased cells. In preparing an antibody conjugated to a liposome, e.g., an immunoliposome, an agent such as a chemotherapeutic or other drug can be entrapped in the liposome for delivery to a target cell.

In some embodiments, the antibody can also have specificity for one or more antigens in addition to ROR1. For example, the antibody of the invention can be engineered (e.g., as a bivalent diabody or a conjugated Fab dimer or trimer) to have specificity for ROR1 and another tumor antigen, e.g., an antigen associated with B-CLL, MCL, Burkitt lymphoma, renal cell carcinoma, colon cancer (e.g., colon adenocarcinoma), or breast cancer (e.g., breast adenocarcinoma). The antibody can be engineered to have specificity for ROR1 and an antigen that promotes activation or targeting of cytotoxic effector cells.

The invention further provides eukaryotic or non-eukaryotic cells that have been recombinantly engineered to produce an antibody of the invention. The eukaryotic or non-eukaryotic cells can be used as an expression system to produce the antibody of the invention. In another embodiment, the invention provides ROR1 targeted immune cells that are engineered to recombinantly express an ROR1 specific antibody of the invention. For example, the invention provides a T-cell engineered to express an antibody of the invention (e.g., an scFv, scFv-Fc, or (scFv)2), which is linked to a synthetic molecule with the following domains: a spacer or hinge region (e.g., a CD28 sequence or a IgG4 hinge-Fc sequence), a transmembrane region (e.g., a transmembrane canonical domain), and an intracellular T-cell receptor (TCR) signaling domain, thereby forming a T-body (or chimeric antigen receptor (CAR)). Intracellular TCR signaling domains that can be included in a T-body (or CAR) include, but are not limited to, CD3ζ, FcR-γ, and Syk-PTK signaling domains as well as the CD28, 4-1BB, and CD134 co-signaling domains. Methods for constructing T-cells expressing a T-body (or CAR) are known in the art. See, e.g., Marcu-Malina et al., *Expert Opinion on Biological Therapy*, Vol. 9, No. 5 (posted online on Apr. 16, 2009).

The invention provides a method of inhibiting cells that express ROR1 (ROR1 cells) by contacting the cells with an antibody of the invention. The antibody can be a naked (unconjugated) antibody or an antibody conjugated to a synthetic molecule, e.g., a cytotoxic, cytostatic, or antiangiogenic agent, a radioisotope, or even to a liposome. The method can be used to inhibit ROR1 cells in vitro or in a subject (i.e., in vivo). The contacted ROR1 cells can be in, for example, a cell culture or animal model of a disorder associated with elevated levels of ROR1. The method is useful, for example, to measure and/or rank (relative to another antibody) the antibody's inhibitory activity for a specific ROR1 cell type. Inhibiting ROR1 cells can include blocking or reducing the activity or growth of ROR1 cells. Inhibiting can also include the killing of ROR1 cells. While the method is not bound by or limited to any particular mechanism of action, inhibitory activity can be mediated by blocking ROR1-mediated signaling or by blocking the signaling of an ROR1 associated receptor. Inhibitory activity can also be mediated by recruitment of immune system effectors that attack ROR1 cells, e.g., by activating constituents of the antibody-dependent cell-mediated cytotoxicity (ADCC) or complement systems.

The invention also provides a method of treating a subject that has, is suspected to have, or is at risk for a disorder associated with elevated levels of ROR1. Generally, the method includes administering a therapeutically effective amount of an isolated antibody of the invention to the subject. The antibody can be any anti-ROR1 antibody of the invention as described herein. Thus, the antibody can be chimeric, humanized, synthetic, F(ab)$_2$, Fv, scFv, IgGΔCH$_2$, F(ab')2, scFv2CH3, Fab, VL, VH, scFv4, scFv3, scFv2, dsFv, Fv, or (scFv)2. In some embodiments, the method includes administering an IgG, an scFv, a dsFv, a F(ab')$_2$, a diabody, or a bivalent antibody. The administered antibody can be conjugated to a synthetic molecule described above, e.g., a cytotoxic, cytostatic, or antiangiogenic agent, a therapeutic radioisotope, or a liposome. An exemplary cytotoxic agent is *Pseudomonas* exotoxin A (PE38). Disorders that can be treated include, for example, B-CLL and MCL. Other disorders associated with elevated ROR1 that can be treated include Burkitt lymphoma, renal cell carcinoma, colon cancer (e.g., colon adenocarcinoma), and breast cancer (e.g., breast adenocarcinoma).

The invention also provides a method of treating a subject that has, is suspected to have, or is at risk for a disorder associated with elevated levels of ROR1 by adoptive transfer of the genetically engineered T-cells described herein, which express an antibody of the invention as a T-body (or CAR) that selectively binds ROR1. Recombinant technology can be used to introduce T-body (or CAR) encoding genetic material into any suitable T-cells, e.g., central memory T-cells from the subject to be treated. The T-cells carrying the genetic material can be expanded (e.g., in the presence of cytokines). The genetically engineered T-cells are transferred, typically by infusion, to the patient. The transferred T-cells of the invention can then mount an immune response against ROR1 expressing cells in the subject. The adoptive transfer method can be used, for example, to treat subjects that have or are suspected to have B-CLL, MCL, Burkitt lymphoma, renal cell carcinoma, colon cancer (e.g., colon adenocarcinoma), or breast cancer (e.g., breast adenocarcinoma).

In some embodiments, the foregoing methods of treatment can further include co-administering a second therapeutic agent for the disorder associated with elevated ROR1. For example, when the disorder to be treated involves an ROR1-expressing cancer, the method can further include co-administration of a cytotoxic, cystostatic, or antiangiogenic agent suitable for treating the cancer. If the cancer is a B-cell malignancy, the method can further include, for example, co-administration of rituximab, alemtuzumab, ofatumumab, or a CHOP chemotherapeutic regimen.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

In another embodiment, the invention provides a method of detecting in a test sample an altered level of ROR1 (e.g., cell surface ROR1), for example, relative to a control. Generally, the method includes contacting a test sample with an antibody of the invention and determining the amount of antibody that selectively binds to material (e.g., cells) in the sample to thereby determine the level of ROR1 in the test sample. A test sample can be from a cell culture or from a test subject, e.g., a plasma or a tissue sample from a subject that has, is suspected to have, or is at risk for a disease or condition associated with elevated ROR1 in a subject. A control level desirably corresponds to the ROR1 level detected using the same antibody in a corresponding sample(s) from one or more control cultures or subjects. Methods of using the antibody of the invention to determine ROR1 levels can include any immunoassay such as immuno- (Western) blotting, enzyme-linked immunosorbent assay (ELISA), and flow cytometry, e.g., fluorescence-activated cell sorting (FACS) analysis.

The method of detection can be used to screen for the presence of a disorder associated with elevated ROR1. The method includes obtaining a sample from a test subject in need of screening, e.g., a subject that has, is suspected to have, or is at risk for a disorder associated with elevated ROR1. The level of ROR1 (e.g., the amount or concentration) in the sample is measured using an antibody of the invention, and the level in the sample is compared to a control level of ROR1. The control level represents, for example, the mean level (e.g., the amount or concentration) in sample(s) from one or, preferably, multiple control group subjects that do not have a disorder associated with elevated ROR1. Alternatively, the control level can correspond to the level or mean level of ROR1 in one or more samples taken from the test subject at one or more prior times, such as when the test subject did not have or did not exhibit, a condition associated with elevated ROR1. A significantly higher level of ROR1 in the test sample relative to the control level is indicative of a disorder associated with elevated ROR1 in the subject.

In subjects such as humans, where cell surface ROR1 expression is largely restricted to embryonic development, a control level of ROR1 can be zero or none. Thus, in some embodiments of the method of the detection provided by the invention, any significant and detectable amount of ROR1 in a test sample can be indicative of a disorder associated with elevated ROR1 in the subject.

Additionally, the method of detection can be used to monitor the progress of a disorder associated with elevated ROR1. The method includes obtaining a sample from a subject in need of screening, e.g., a subject having been diagnosed or suspected to have a disorder associated with elevated ROR1. The level of ROR1 in the sample is measured using an antibody of the invention, and the level in the sample is compared to a control level corresponding to the level or mean level of ROR1 in one or more samples taken from the test subject at one or more prior times. Levels of ROR1 that are significantly elevated or decreased relative to control indicate that the subject's disorder is deteriorating or improving, respectively.

The foregoing method of detection can be used to screen for the presence or to monitor the progress of disorders including, for example, B-CLL, MCL, Burkitt lymphoma, renal cell carcinoma, colon cancer (e.g., colon adenocarcinoma), and breast cancer (e.g., breast adenocarcinoma).

The invention provides a method for screening a subject for an altered level of ROR1. Generally, the method includes administering to the subject an antibody of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the method includes determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk for an ROR1-expressing tumor, such as B-CLL, MCL, Burkitt lymphoma, renal cell carcinoma, tumor of the colon (e.g., colon adenocarcinoma), or breast tumor (e.g., breast adenocarcinoma), and the method is used to screen for or detect the presence of the tumor. In another embodiment, the method can be used to monitor the size or density of an ROR1-expressing tumor over time, e.g., during a course of treatment.

The invention also provides a pharmaceutical composition comprising an antibody as described above and a pharmaceutically acceptable carrier. Pharmaceutical compositions can be prepared from any of the antibodies described herein. Exemplary compositions include one or more of a chimeric antibody having SEQ ID NO: 1 (light chain) and/or SEQ ID NO: 2 (heavy chain), a chimeric antibody having SEQ ID NO: 3 (light chain) and/or SEQ ID NO: 4 (heavy chain), and a chimeric antibody having SEQ ID NO: 5 (light chain) and/or SEQ ID NO: 6 (heavy chain). Another exemplary composition comprises a humanized antibody having one, two, three, four, five, or six CDRs selected from the group consisting of SEQ ID NOs: 31-48. In preferred embodiments, however, the antibody includes three CDR sequences of the same light or heavy chain, e.g., SEQ ID NOs: 31-33, SEQ ID NOs: 34-36; SEQ ID NOs: 37-39; SEQ ID NOs: 40-42; SEQ ID NOs: 43-45; or SEQ ID NOs: 46-48. In more preferred embodiments, the composition includes an antibody having six CDR sequences of the same antibody, e.g., (a) SEQ ID NOs: 31-33 and SEQ ID NOs: 40-42; (b) SEQ ID NOs: 34-36 and SEQ ID NOs: 43-45; or (c) SEQ ID NOs: 37-39 and SEQ ID NOs: 46-48. Still another exemplary pharmaceutical composition includes a dsFv fragment, which can include one or more modifications to the amino acid sequence as appropriate and understood by one of ordinary skill in the art.

The composition of the invention comprises a carrier for the antibody, desirably a pharmaceutically acceptable carrier. The pharmaceutically acceptable carrier can be any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. "Pharmaceutically acceptable" materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

The pharmaceutical composition can contain suitable buffering agents, including, for example, acetic acid in a salt, citric acid in a salt, boric acid in a salt, and phosphoric acid in a salt. The pharmaceutical composition also optionally can contain suitable preservatives, such as benzalkonium chloride, chlorobutanol, parabens, and thimerosal.

The pharmaceutical composition can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono- or di-glycerides. In addition, fatty acids such as oleic acid can be used in the preparation of injectables. Carrier formulations suitable for oral, subcutaneous, intravenous, intramuscular, etc. administrations can be found in *Remington's Pharmaceutical Sciences*, Mack Publishing Co., Easton, Pa.

The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The term "subject" is used herein, for example, in connection with therapeutic and diagnostic methods, to refer to human or animal subjects. Animal subjects include, but are not limited to, animal models, such as, mammalian models of conditions or disorders associated with elevated ROR1 expression such as B-CLL, MCL, Burkitt lymphoma, renal cell carcinoma, colon cancer, (e.g., colon adenocarcinoma), and breast cancer (e.g., breast adenocarcinoma).

The invention also provides kits suitable for carrying out the methods of the invention. Typically, a kit comprises two or more components required for performing a therapeutic or detection method of the invention. Kit components include, but are not limited to, one or more antibodies of the invention, appropriate reagents, and/or equipment.

A kit can comprise an antibody of the invention and an immunoassay buffer suitable for detecting ROR1 (e.g. by ELISA, flow cytometry, magnetic sorting, or FACS). The kit may also contain one or more microtiter plates, standards, assay diluents, wash buffers, adhesive plate covers, magnetic beads, magnets, and/or instructions for carrying out a method of the invention using the kit. The kit can include an antibody of the invention bound to a substrate (e.g., a multi-well plate or a chip), which is suitably packaged and useful to detect ROR1. In some embodiments, the kit includes an antibody of the invention that is conjugated to a label, such as, a fluorescent label, a biologically active enzyme label, a luminescent label, or a chromophore label. The kit can further include reagents for visualizing the conjugated antibody, e.g., a substrate for the enzyme. In some embodiments, the kit includes an antibody of the invention that is conjugated to a contrast agent and, optionally, one or more reagents or pieces of equipment useful for imaging the antibody in a subject.

Generally the antibody of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use, or they can be provided at the concentration of use. For use of the antibody of the invention in vivo, single dosages may be provided in sterilized containers having the desired amount and concentration of components.

The following examples further illustrate the invention but, of course, should not be construed as in any way limiting its scope.

Example 1

This example demonstrates the preparation of monoclonal Fab antibodies with specificity for ROR1.

The three extracellular domains of human ROR1 were expressed alone (hROR1ECD) or as a fusion protein with the Fc domain of human IgG1 (Fc-hROR1) (FIG. 1). Purified Fc-hROR1 and hROR1ECD were used to immunize and boost two groups of rabbits of the b9 allotype to prepare chimeric rabbit/human Fab libraries as described in Popkov, *J. Mol. Biol.*, 325(2): 325-335 (2003). A total of six b9 allotype rabbits were used. Four rabbits were immunized and boosted three times with 100 µs Fc-hROR1, using Freund's complete and incomplete adjuvant (Sigma-Aldrich; St. Louis, Mo.) for two rabbits and TiterMax adjuvant (Sigma-Aldrich) for the other two rabbits. Library R was based on these four rabbits. Library Y was based on two additional rabbits that were immunized with 100 µg Fc-hROR1 and boosted three times with 100 µg hRORECD using Ribi (Sigma-Aldrich) adjuvant. Spleen and bone marrow from both femurs of each rabbit were collected five days after the final boost and processed for total RNA preparation and RT-PCR amplification of rabbit $V_\kappa$, $V_\lambda$, and $V_H$ encoding sequences using established primer combinations and protocols as described in Rader, *Methods Mol. Biol.*, 525: 101-128, xiv (2009). Rabbit $V_L$/human $C_\kappa$/rabbit $V_H$ segments were assembled in one fusion step based on 3-fragment overlap extension PCR, digested with SfiI, and cloned into pC3C. Transformation of *E. coli* strain XL1-Blue (Stratagene; La Jolla, Calif.) by electroporation yielded approximately $2.5 \times 10^8$ and $1.4 \times 10^8$ independent transformants for libraries R and Y, respectively.

Using VCSM13 helper phage (Stratagene), the phagemid libraries were converted to phage libraries and selected by panning against immobilized protein. Libraries R and Y were selected in parallel by four rounds of panning against hROR1ECD. In addition, library Y was selected by three rounds of panning on hROR1ECD followed by a final panning round on Fc-hROR1. During the panning against immobilized Fc-hROR1, unspecific polyclonal human IgG antibodies (Thermo Scientific; Rockford, Ill.) were added as decoy at a final concentration of 1 µg/µL. Supernatants of IPTG-induced selected clones were analyzed by ELISA using immobilized hROR1ECD and Fc-hROR1 and by flow cytometry using HEK 293F cells stably transfected with human ROR1 (Kwong et al., *J. Mol. Biol.*, 384(5): 1143-56 (2008)). Rat anti-HA mAb 3F10 conjugated to horse radish peroxidase (Roche) was used in ELISA at a concentration of 50 ng/mL. The absorbance was measured at 405 nm using a VersaMax microplate reader (Molecular Devices; Sunnyvale, Calif.) and SoftMax Pro software (Molecular Devices). Rat anti-HA mAb 3F10 conjugated to biotin was used in flow cytometry at a concentration of 5 µg/mL. Florescence intensity was analyzed using a FACSCalibur instrument (BD Biosciences) and FlowJo analytical software (TreeStar, Ashland, Oreg.).

Repeated clones were identified by DNA fingerprinting with AluI, and the $V_L$ and $V_H$ sequences of unique clones were determined by DNA sequencing as described in Rader, *Methods Mol. Biol.*, 525: 101-128, xiv (2009).

As summarized in Table 1, seven different chimeric rabbit/human Fab clones that bound to hROR1ECD were identified.

Of the seven clones provided in Table 1, three clones (designated R11, R12, and Y31) also bound to Fc-hROR1 and cell surface human ROR1 expressed by stably transfected HEK 293F cells as described in Kwong et al., *J. Mol. Biol.*, 384(5): 1143-56 (2008). The expression cassettes encoding Fab R11, R12, and Y31 were transferred by SfiI cloning into a Fab-(His)$_6$ expression cassette in vector pET11a with an IPTG-inducible T7 promoter (Stahl et al., *J. Mol. Biol.*, 397(3): 697-708 (2010)) to remove the HA tag and gene III fragment encoding sequences of pC3C (Hofer et al., *J. Immunol. Methods*, 318(1-2): 75-87 (2007)), and to add a C-terminal (His)$_6$ tag. Following transformation into *E. coli* strain BL21-CodonPlus(DE3)-RIL (Stratagene) and expression through IPTG induction, Fab R11, R12, and Y31 were purified from bacterial supernatants by Immobilized Metal Ion Affinity Chromatography using a 1-mL HisTrap column (GE Healthcare) as described in Kwong, K. Y. and C. Rader, *Curr. Protoc. Protein Sci.*, Chapter 6: Unit 6, 10 (2009), followed by gel filtration chromatography using a Superdex 200 10/300 GL column with an ÄKTA FPLC instrument (GE Healthcare). The quality and quantity of purified Fab was analyzed by SDS-PAGE and absorbance at 280 nm, respectively, and the variable domains of R11, R12, and Y31 were sequenced.

As depicted in FIG. 2, the diverse amino acid sequences of both frameworks and complementarity determining regions of the rabbit variable domains of R11, R12, and Y31 revealed unrelated $V_\kappa$ (R11, Y31), $V_\lambda$ (R12), and $V_H$ germlines.

These results demonstrate the production of Fab antibodies to ROR1.

Example 2

This example demonstrates the preparation of monoclonal IgG antibodies with specificity for ROR1.

For the expression of R11, R12, and Y31 in IgG1 format, vector PIGG was used as described in Popkov et al., *J. Mol. Biol.*, 325(2): 325-335 (2003). In this vector, γ1 heavy and κ light chains are expressed by an engineered bidirectional CMV promoter cassette. The $V_H$ encoding sequences of Fab R11 and R12 were PCR amplified using primers R11-VH-5'(gaggaggagctcactcccagteggtgaaggagtccga [SEQ ID NO: 49]) and P14-VH-5' (Hofer et al., *J. Immunol. Methods*, 318(1-2): 75-87 (2007)), respectively, in combination with R11-12-VH-3'(ccgatgggccatggtggaggctgaggagatggtgaccagggtgcctggtccccagatg [SEQ ID NO: 50]), and cloned via ApaI/SacI into PIGG. The light chain encoding sequences of

TABLE 1

Panel of chimeric rabbit/human Fab selected by phage display.

| Clone[1] | Library | Panning rounds hROR1 ECD | Panning rounds Fc-hROR1 | Repeats | Binding hROR1 ECD[2] | Binding Fc-hROR1[2] | Binding HEK 293F/HROR1[3] |
|---|---|---|---|---|---|---|---|
| R11 | R | 4 | 0 | 26/31 | ++ | ++ | + |
| R12 | R | 4 | 0 | 1/31 | ++ | ++ | ++ |
| Y4 | Y | 4 | 0 | 2/31 | ++ | − | − |
| Y13 | Y | 4 | 0 | 14/31 | ++ | − | − |
| Y14 | Y | 4 | 0 | 2/31 | + | − | − |
| Y27 | Y | 4 | 0 | 13/31 | ++ | − | − |
| Y31 | Y | 3 | 1 | 4/4 | + | + | + |

[1]Defined by unique DNA fingerprint and sequence.
[2]As measured by ELISA.
[3]As measured by flow cytometry.

Fab R11 and R12 were PCR amplified using primers P14-light-5' (Hofer et al., *J. Immunol. Methods,* 318(1-2): 75-87 (2007)) and R12-light-5'(gaggagaagcttgttgctctggatctctggt-gcctacggggaactcgtgctgactcagtc [SEQ ID NO: 51]), respectively, in combination with primer C-kappa-3' (Hofer et al., *J. Immunol. Methods,* 318(1-2): 75-87 (2007)), and cloned via HindIII/XbaI into PIGG with the corresponding heavy chain encoding sequence.

The resulting chimeric rabbit/human light chain of R12 is composed of a rabbit $V_\lambda$ and a human $C_\kappa$ domain. The $V_H$ encoding sequence of Fab Y31 was PCR amplified using primers M5-VH-5' and M5-VH-3' (Hofer et al., *J. Immunol. Methods,* 318(1-2): 75-87 (2007)), and cloned via ApaI/SacI-ligation into PIGG. To remove an internal HindIII site by silent mutation, two fragments of the light chain encoding sequence of Fab Y31 were PCR amplified using primers P14-light-5' in combination with Y31-light-3'(attggatg-cataatagatcagtagcttgggaggctg [SEQ ID NO: 52]) and Y31-light-5'(aaccagggcagcctcccaagctactgatct [SEQ ID NO: 53]) in combination with C-kappa-3', fused by overlap extension PCR using primers P14-light-5' and C-kappa-3', and cloned via HindIII/XbaI into PIGG with the corresponding heavy chain encoding sequence. The resulting PIGG-R11, PIGG-R12, and PIGG-Y31 plasmids were transiently transfected into human HEK 293F cells (Invitrogen; Carlsbad, Calif.) with 293 fectin (Invitrogen), and purified by 1-mL recombinant Protein A HiTrap column (GE Healthcare, Piscataway, N.J.) as described in Hofer et al., *J. Immunol. Methods,* 318(1-2): 75-87 (2007). The quality and quantity of purified IgG1 was analyzed by SDS-PAGE and $A_{280}$ absorbance, respectively. These results demonstrate the production of IgG antibodies to ROR1.

Example 3

This example demonstrates specificity and epitope mapping of Fab and IgG chimeric rabbit/human antibodies to ROR1.

Figure 3:
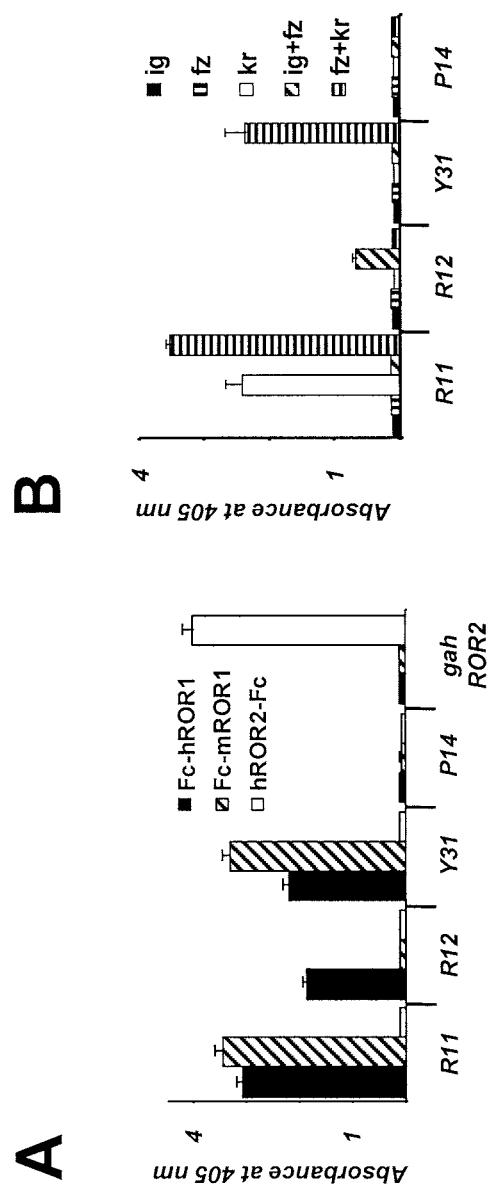

R11, R12, and Y31 were prepared as Fab and IgG. Fab regions were prepared as described in Example 1. IgG chimeric rabbit/human antibodies were prepared as described in Example 2. The specificity of the purified Fab and IgG1 was probed by ELISA with an extended panel of recombinant ROR1 proteins that included Fc-hROR1, its mouse analogue Fc-mROR1, and five Fc fusion proteins with only one or two extracellular domains of human ROR1 as shown in FIG. 1. Also included was commercially available hROR2-Fc (R&D Systems; Minneapolis, Minn.). Chimeric rabbit/human Fab and IgG1 P14 against NgR2 (Hofer et al., *J. Immunol. Methods,* 318(1-2): 75-87 (2007)) was used as negative control. Fab (data not shown) and IgG1 (FIG. 3) revealed identical binding patterns. As shown in FIG. 3A, IgG1 R11, R12, and Y31 bound to human ROR1, but not to human ROR2. In addition, IgG1 R11 and Y31 were found to be cross-reactive with mouse ROR1. The binding of IgG1 R11, R12, and Y31 to only one or two extracellular domains of human ROR1 (FIG. 3B) confirmed the recognition of three different epitopes. In selectively recognizing Fc-hROR1kr and Fc-hROR1kr+fz, IgG1 R11 was the only mAb that mapped to a single domain. In contrast, IgG1 R12 and Y31 selectively recognized Fc-hROR1ig+fz and Fc-ROR1fz+kr, respectively, but not any of the single domains, thereby indicating that the epitopes of these mAbs either are located in the region that links two neighboring domains, i.e. at the conjunction of Ig and Fz domains in case of R12 and at the conjunction of Fz and Kr domains in case of Y31, or bind to conformational epitopes that require the presence of these two neighboring domains.

The three epitopes of IgG1 R11, R12, and Y31 were found to encompass a large portion of the extracellular region of human ROR1. To investigate the therapeutic implications of membrane distal and proximal binding of anti-ROR1 mAbs, the independence of the three epitopes was also analyzed by surface plasmon resonance using a Biacore X100 (GE Healthcare, Piscataway, N.J.) instrument. Studies were performed using surface plasmon resonance for the measurement of the affinities of Fab R11, R12, and Y31 and the virtual affinities of IgG1 R11, R12, and Y31 to Fc-hROR1 and Fc-mROR1, as well as for epitope mapping. For affinity measurements, CM5 sensor chips were activated for immobilization with 1-ethyl-3-(3-dimethylaminopropyl)carbodiimide hydrochloride and N-hydroxysuccinimide. Fc-hROR1 and Fc-mROR1 fusion proteins in 10 mM sodium acetate (pH 5.0) were immobilized at a density of 669 resonance units (RU) for Fc-hROR1 and 429 RU for Fc-mROR1 in two flow cells on separate sensor chips. Subsequently, the sensor chips were deactivated with 1M ethanolamine hydrochloride (pH 8.5). Each sensor chip included an empty flow cell for instantaneous background depletion. All binding assays used 1×HBS-EP+ running buffer (10 mM HEPES, 150 mM NaCl, 3 mM EDTA (pH 7.4), and 0.05% (v/v) Surfactant P20) and a flow rate of 30 μL/min. Fab and IgG1 R11, R12, and Y31 were injected at five or six different concentrations ranging from 1.5 to 100 nM in duplicates. The sensor chips were regenerated with glycine-HCl (pH 2.0) without any loss of binding capacity. Calculation of association ($k_{on}$) and dissociation ($k_{off}$) rate constants was based on a 1:1 Langmuir binding model. The equilibrium dissociation constant ($K_d$) was calculated from $k_{off}/k_{on}$. For epitope mapping studies, Fc-hROR1 was immobilized on a CM5 sensor chip at a density of 219 RU. IgG1 R11, R12, and Y31 were prepared as 300 nM solution in 1×HBS-EP+ running buffer. In the first cycle, IgG1 R11 was injected first, followed by a mixture of IgG1 R11 and R12, followed finally by a mixture of IgG1 R11, R12, and Y31. IgG1 R11 or IgG1 R11 in combination with IgG1 R12 were included in these mixtures to prevent signal loss due to dissociation. In the second cycle the injection order was R11, R11+Y31, and R11+Y31+R12. Analogously, R12 was injected first in the third and fourth cycle, and Y31 was injected first in the fifth and sixth cycle. RU increases that exceeded the values found for IgG1 R11, R12, and Y31 alone indicated independent epitopes that allow simultaneous binding.

Figure 4:
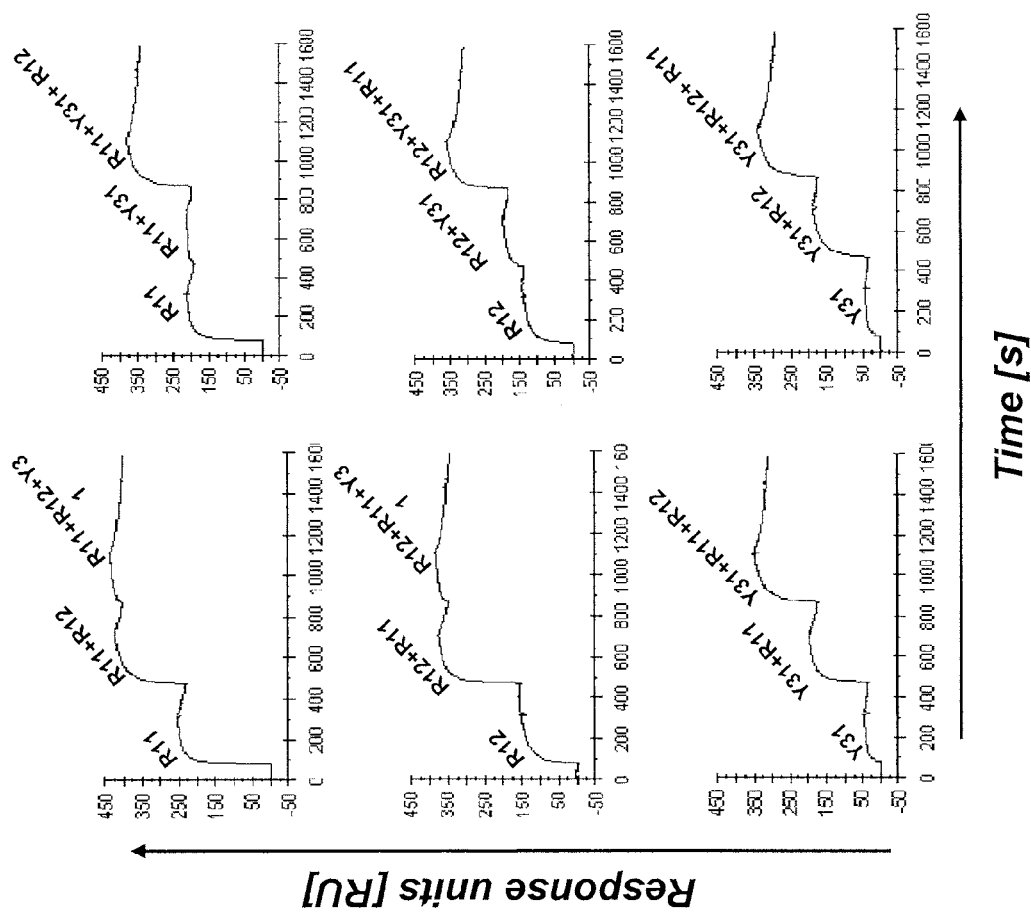

As shown in FIG. 4, IgG1 R11 and R12 were found to bind simultaneously and independently to Fc-hROR1 regardless of the sequence of injection. By contrast, IgG1 R11, but not IgG1 R12, was found to block the binding of IgG1 Y31 when injected first or compete with the binding of IgG1 Y31 when injected second. Surface plasmon resonance also revealed the simultaneous binding of Fab R11 and R12 to Fc-hROR1 (data not shown).

These results demonstrate that the epitopes of R11 in the Kr domain and Y31 at the conjunction of Fz and Kr domains partially overlap, whereas R12 binds to an independent epitope at the conjunction of Ig and Fz domains.

Example 4

This example demonstrates various binding properties of mAbs R11, R12, and Y31 in IgG and Fab format.

Figure 5:
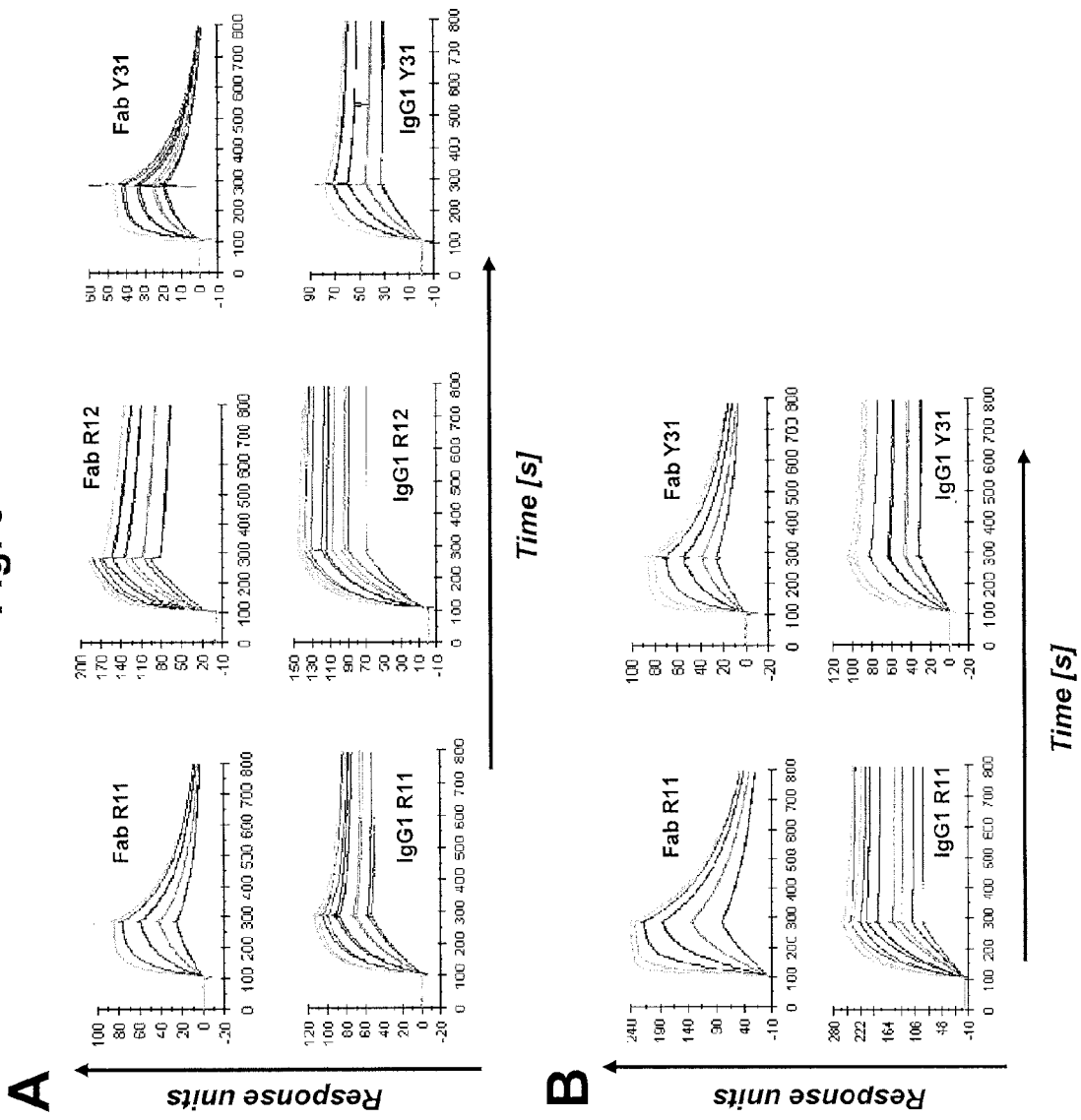

Surface plasmon resonance with the Biacore X100 instrument (GE Healthcare, Piscataway, N.J.), as described in Example 3, was used to measure the affinity and avidity of mAbs R11, R12, and Y31 in Fab and IgG1 format, respectively, as shown in Table 2 and FIG. 5. Fab R12 was found to be the strongest binder with an affinity of 0.56 nM to Fc-hROR1. Fab R11 and Y31 revealed affinities of 2.7 and 8.8 nM, respectively. An approximately twenty-fold slower dissociation rate was determined for Fab R12, whereas Fab R11 was found to have a faster association rate. Conversion from monovalent Fab to bivalent IgG1 increased the virtual affinity of R11, R12, and Y31 by factor 14, 5, and 12, respectively; all three IgG1 revealed subnanomolar avidity. Confirming the ELISA data, R11 and Y31 revealed comparable affinities and avidities for Fc-hROR1 and Fc-mROR1, indicating that their epitopes are entirely conserved between human and mouse ROR1. By contrast, R12 did not reveal detectable binding to Fc-mROR1.

TABLE 2

| MAb | Antigen | $k_{on} (10^5)$ $(M^{-1}s^{-1})$ | $k_{off} (10^{-4})$ $(s^{-1})$ | $K_d$ (nM) |
|---|---|---|---|---|
| Fab R11 | Fc-hROR1 | 20.4 | 54.7 | 2.7 |
|  | Fc-mROR1 | 16.9 | 50.4 | 3.0 |
| IgG1 11 | Fc-hROR1 | 19.4 | 3.6 | "0.19" |
|  | Fc-mROR1 | 9.9 | 3.0 | "0.30" |
| Fab R11 | Fc-hROR1 | 5.5 | 3.1 | 0.56 |
|  | Fc-mROR1 | no binding | no binding | no binding |
| IgG1 R12 | Fc-hROR1 | 5.5 | 0.62 | "0.11" |
|  | Fc-mROR1 | no binding | no binding | no binding |
| Fab Y31 | Fc-hROR1 | 8.5 | 75.2 | 8.8 |
|  | Fc-mROR1 | 9.1 | 38.3 | 4.2 |
| IgG1 Y31 | Fc-hROR1 | 4.9 | 3.5 | "0.71" |
|  | Fc-mROR1 | 5.4 | 2.4 | "0.44" |

Figure 6:
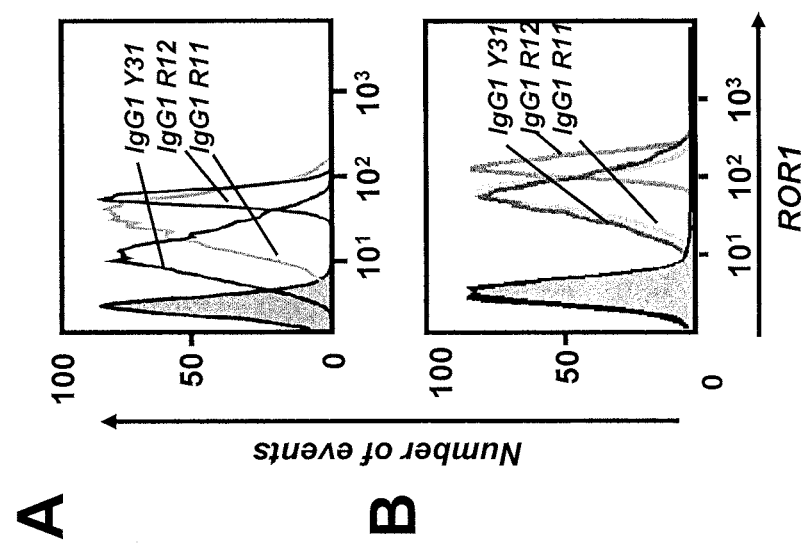
Figure 7:
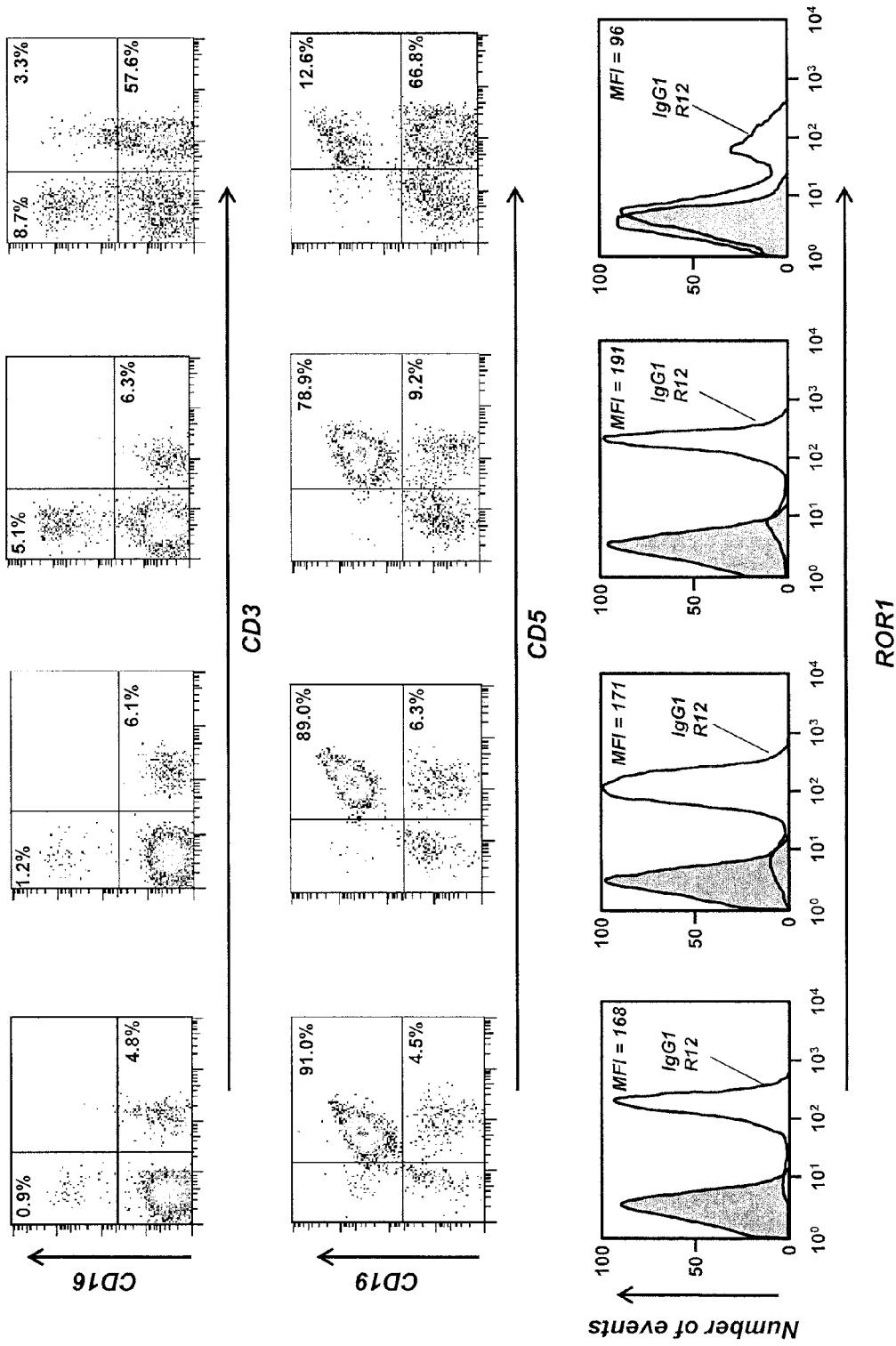

As described in Example 1, Fab R11, R12, and Y31 recognized cell surface human ROR1 expressed by stably transfected HEK 293F cells. Flow cytometry was used to validate the selective binding of IgG1 R11, R12, and Y31 to JeKo-1 and HBL-2 cells (FIGS. 6A-B). JeKo-1 and HBL-2 are human mantle cell lymphoma cell lines that express ROR1 at similar levels as primary human CLL cells. Cells were stained using standard flow cytometry methodology. Briefly, for anti-ROR1 Fab, cells were stained with unpurified or purified Fab on ice for 1 h. After washing twice with ice-cold flow cytometry buffer (PBS containing 1% (v/v) FBS), cells were incubated with 5 µg/mL of biotinylated rat anti-HA mAb 3F10 (Roche) in flow cytometry buffer on ice for 1 h, washed as before, and stained with PE-streptavidin (BD Biosciences) on ice for 30 min. For anti-ROR1 IgG1, cells were first blocked with hIgG at room temperature for 20 min, then incubated on ice for 1 h with biotinylated anti-ROR1 IgG1 alone (for HEK 293F/hROR1, JeKo-1, and HBL-2 cells) or in combination with FITC-CD19/APC-CD5 (BD Biosciences; Franklin Lakes, N.J.) (for PBMC from untreated CLL patients). After washing twice with ice-cold flow cytometry buffer, cells were stained with PE-streptavidin on ice for 30 min. Propidium iodide (PI) was added to a final concentration of 5 µg/mL to exclude dead cells from analysis. Cells were analyzed using a FACSCalibur instrument (BD Biosciences) and FlowJo analytical software (TreeStar, Ashland, Oreg.).

Human anti-tetanus toxoid mAb TT11 in IgG1 format (Kwong et al., *J. Mol. Biol.*, 384(5): 1143-56 (2008)) was used as a negative control, as shown in Table 3, which sets forth the data on flow cytometry binding of IgG1 R11, R12, and Y31 to primary CLL cells from one representative patient (shown in units of mean fluorescence intensity (MFI)).

TABLE 3

|  | 0.01 µg/mL | 0.1 µg/mL | 1 µg/mL | 5 µg/mL | 10 µg/mL |
|---|---|---|---|---|---|
| IgG1 R1 | Not determined | 6.6 | 18.1 | 64.9 | 137.7 |
| IgG1 R12 | 36.4 | 89.4 | 97.9 | 121.8 | Not determined |
| IgG1 Y31 | Not determined | 5.4 | 8.3 | 21.6 | 58.9 |
| IgG1 TT11 | 4.9 | 4.8 | 7.2 | 7.3 | 7.3 |

IgG1 R12 demonstrated strong and homogeneous binding at concentrations as low as 0.01 µg/mL (67 µM), confirming its subnanomolar avidity found by surface plasmon resonance. By contrast, the binding of IgG1 R11 and, in particular, Y31 was somewhat weaker and more heterogeneous. This pattern correlates with the different avidities found for the three mAbs, and is supported by the accessibility of the three different epitopes on cell surface ROR1. The presumed membrane distal epitope of R12 at the conjunction of Ig and Fz domains improve access for the bulky IgG1 format as compared with the presumed membrane proximal epitope of R11 and Y31 in the Kr domain and at the conjunction of Fz and Kr domains, respectively. In fact, conversion of R11 to the less bulky scFv-Fc format (~100 kDa; two polypeptide chains) demonstrated significantly stronger binding at lower concentrations compared to the IgG1 format (~150 kDa; four polypeptide chains) (data not shown).

The binding of IgG1 R11, R12, and Y31 was analyzed against PBMC prepared from five untreated CLL patients. Chimeric rabbit/human IgG1 P14 against NgR2 served as negative control. Representative flow cytometry plots from one CLL patient as compared to negative controls are shown in FIG. 6B. Consistent with the results of Baskar et al., *Clin. Cancer Res.*, 14(2): 396-404 (2008) (goat anti-human ROR1 pAbs), IgG1 R11, R12, and Y31 selectively bound to CLL cells (CD5+ CD19+), but not to normal B cells (CD5− CD19+), T cells (CD5+ CD19−), and CD5− CD19− PBMC from untreated CLL patients. The pattern of binding to primary CLL cells was similar to that noted for the JeKo-1 cell line, namely strong and homogeneous binding of IgG1 R12, and weaker and more heterogeneous binding of IgG1 R11 and Y31. Additional flow cytometry plots showing the binding of IgG1 R12 to PBMC prepared from an additional four CLL patients are shown in FIG. 7A-D. Gating for normal NK cells, T cells, and B cells in these CLL patients further confirmed the specificity of IgG1 R12 for CLL cells.

The foregoing results demonstrate that IgG1 R11, R12, and Y31 have subnanomolar avidity for ROR1 and can be used to specifically distinguish (i) tumor cells obtained from lymphoma patients from (ii) normal B-cells taken from healthy subjects.

Example 5

This example evaluates the complement-dependent cytotoxic (CDC) properties of chimeric rabbit/human anti-ROR1 antibodies.

As target cells, JeKo-1 and HBL-2 cells or cryopreserved PBMC from untreated CLL patients were harvested, washed, and resuspended in RPMI 1640 containing 10% (v/v) FBS, 100 U/mL penicillin, and 100 µg/mL streptomycin, and distributed into 96-well U-bottom plates (Corning; Corning, N.Y.) at a density of 1×10$^5$ cells/well. After incubation for 1 h on ice with 20 µg/mL IgG1 R11, R12, Y31, and P14 (negative control), as well as unspecific polyclonal human IgG (Thermo Scientific) as a further negative control and rituximab (Genentech; South San Francisco, Calif.) as a positive control, the cells were harvested, washed once with PBS to remove unbound antibodies, and incubated with 20% complement from 3-4-week-old rabbits (Pel-Freez; Rogers, A R) for 2 h at 37° C. in 5% $CO_2$. After adding PI to a final concentration of 5 µg/mL, dead cells were detected by PI accumulation using a FACSCalibur instrument and FlowJo analytical software.

Figure 8:
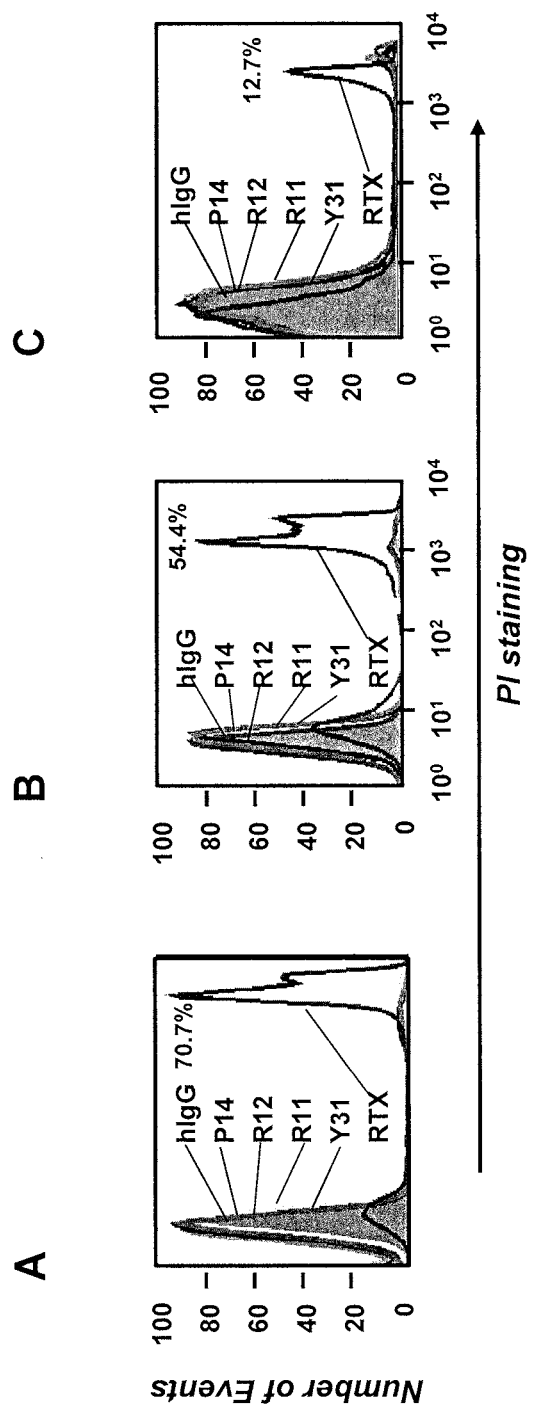
FIG. 8A is a graph that depicts flow cytometry results of IgG1 R11, R12, and Y31 in comparison to IgG1 P14 (negative control), unspecific polyclonal human IgG (hIgG; negative control), and rituximab (RTX; positive control) toward JeKo-1 cells in the presence of rabbit complement. PI staining indicating cytotoxicity was observed for rituximab only.
FIG. 8B is a graph that depicts flow cytometry results of IgG1 R11, R12, and Y31 in comparison to IgG1 P14 (negative control), unspecific polyclonal human IgG (hIgG; negative control), and rituximab (RTX; positive control) toward HBL-2 cells in the presence of rabbit complement. PI staining indicating cytotoxicity was observed for rituximab only.
FIG. 8C is a graph that depicts flow cytometry results of IgG1 R11, R12, and Y31 in comparison to IgG1 P14 (negative control), unspecific polyclonal human IgG (hIgG; negative control), and rituximab (RTX; positive control) toward PBMC from untreated CLL patients in the presence of rabbit complement. PI staining indicating cytotoxicity was observed for rituximab only.

Whereas rituximab mediated potent CDC, none of the other antibodies revealed cytotoxicity above background (FIG. 8), and neither did a mixture of IgG1 R11 and R12 or rabbit anti-human ROR1 IgG pAbs purified from the serum of our immunized rabbits (data not shown).

These findings do not indicate that ROR1 is a suitable antigen for mediating CDC by mAbs or pAbs in IgG format.

Example 6

This example evaluates the antibody-dependent cellular cytotoxicity (ADCC) properties of chimeric rabbit/human anti-ROR1 antibodies.

ADCC was assayed in a bioluminescent protease release assay (Glo Cytotoxicity Assay; Promega, Madison, Wis.) using the manufacturer's protocol with minor modifications. NK cells from healthy volunteers prepared from apheresis blood were used as effector cells. JeKo-1 and HBL-2 cells or cryopreserved PBMC from untreated CLL patients prepared described in Example 5 were used as target cells and distributed into 96-well U-bottom plates at a density of $1×10^4$ cells/well. The target cells were preincubated for 1 h at 37° C. with serially diluted (from 20 to 0.02 µg/mL) IgG1 R11, R12, Y31, TT11 (negative control), and rituximab (positive control). Without washing, effector cells were added (100 µL/well) at an effector-to-target cell ratio of 20:1 or 25:1 and incubated for 24 h at 37° C. in 5% $CO_2$. After centrifugation, 50 µL/well of supernatant was transferred to a 96-well Costar 3610 white tissue culture plate followed by addition of 25 µL/well CytoTox-Glo cytotoxicity assay reagent (Promega, Madison, Wis.). After 15 min at room temperature, luminescence was measured with a Spectra Max M5 microplate reader (Molecular Devices, Sunnyvale, Calif.). The percentage of specific cytotoxicity was calculated according to the formula: Percent specific cytotoxicity=$100×(EX-E_{spon}-T_{spon})/(T_{max}-T_{spon})$, where EX represents the release from experimental wells, $E_{spon}$ is the spontaneous release of effector cells alone, $T_{spon}$ is the spontaneous release of target cells alone, and $T_{max}$ is the maximum release from target cells lysed in 30 µg/mL digitonin. Data were computed as mean±standard deviation of triplicates.

Rituximab-mediated ADCC demonstrated similar potency against JeKo-1 and HBL-2 cells (FIG. 9A). This ADCC activity was robust over a concentration range from 0.02 µg/mL to 20 µg/mL (FIG. 9C). By contrast, ADCC activity was detectable for IgG1 R12 only at or above 5 µg/mL (FIGS. 9A, C), IgG1 R11 and Y31 were not significantly different from the negative control. Similar results are shown in FIG. 9B, which provides ADCC results against PBMC of untreated CLL patients.

These results show that IgG R12 has weak ADCC activity but do not indicate ADCC activity for IgG1 R11 or Y31.

Example 7

This example provides analysis of the role of internalization or dissociation in the inability of IgG1 R11, R12, and Y31 to mediate CDC and ADCC.

Using a 96-well U-bottom plate, $3×10^6$ cryopreserved PBMC from untreated CLL patients were first blocked with 100 µg/mL unspecific polyclonal human IgG at room temperature for 20 min, then stained with 10 µg/mL biotinylated IgG1 R11 and Y31, or 1 µg/mL biotinylated IgG1 R12 on ice for 1 h. After washing three times with flow cytometry buffer to remove unbound antibody, the cells were either left on ice or incubated at 37° C. for 15 min, 30 min, 1 h, and 2 h to facilitate internalization. In addition, the cells were incubated at 37° C. for 2 h in the presence of 10 µM phenylarsine oxide (Sigma-Aldrich) to inhibit internalization. Subsequently, the cells were washed once with flow cytometry buffer and incubated with PE-streptavidin on ice for 30 min. After three final washes with flow cytometry buffer, the mean fluorescence intensity (MFI) of the cells was measured using a FACSCalibur instrument and FlowJo analytical software.

MFI reduction can be explained by internalization or dissociation or a combination of both. The percentage of MFI reduction was calculated for each mAb relative to the unspecific polyclonal human IgG control ($MFI_{background}$) and mAb maintained on ice ($MFI_{max}$) by using the formula $[(MFI_{max}-MFI_{background})-(MFI_{experimental}-MFI_{background})]/(MFI_{max}-MFI_{background})×100$.

Human ROR1 has previously been shown to mediate internalization of polyclonal goat anti-human ROR1 IgG by a route that can be completely blocked by endocytosis inhibitor phenylarsine oxide (Baskar et al., *Clin. Cancer Res.*, 14(2): 396-404 (2008)). MFI reduction was noted for all three IgG1 after 2 h (FIG. 10B). In case of IgG1 R11 and R12, phenylarsine oxide completely blocked MFI reduction, revealing internalization as the dominating factor. By contrast, dissociation contributed to the continuous disappearance of IgG1 Y31 from the cell surface (FIG. 10B).

IgG1 R12 internalized more slowly than IgG1 R11 with peaks at 20-25% after 2 h compared to 50-55%.

These results provide evidence that the more durable presence of IgG1 R12 at the cell surface contributes to the weak ADCC activity noted for IgG1 R12 which was not detected for IgG1 R11 and Y31.

Example 8

This example demonstrates the construction and characterization of a disulfide stabilized fragment (dsFv) of chimeric rabbit/human anti-ROR1 antibodies R11, R12, and Y31 fused to an immunotoxin.

A dsFv fragment of mAb R11, R12, or Y31 (dsFv) is generated and fused to a 38-kDa fragment of *Pseudomonas* exotoxin A (PE38) generally according to methods described in Pastan et al., *Methods Mol. Biol.*, 248: 503-518 (2004). The original VH and VL coding sequences of R11, R12, or Y31 (see FIG. 2) are altered as necessary to prepare a dsFv fragment. The altered VH coding sequence is subcloned in-frame with a PE38 coding sequence in a pRB98 vector carrying a chloramphenicol resistance gene (the vector is described in Kreitman et al., in *Drug Targeting*, Francis et al., Eds., Vol. 25, pp. 215-226, Humana Press Inc, Totowa, N.J., 2000). Altered VH and VL chains are separately expressed in *E. coli*, and the resulting proteins are harvested and solubilized. The VH and VL are refolded together to form dsFv-PE38 fusion immunotoxin, which is purified by ion-exchange and gel filtration chromatography as described in Pastan et al., supra, 2004.

The resulting recombinant dsFv-PE38 immunotoxin conjugates are evaluated by flow cytometry and compared to chimeric rabbit/human anti-ROR1 antibodies R11, R12, and Y31 for their ability to bind to the human ROR1-expressing mantle cell lymphoma cell lines JeKo-1 and HBL-2. JeKo-1 and HBL-2 cell binding by mAbs R11, R12, and Y31 is detected using a goat anti-mouse IgG polyclonal antibody (pAb) conjugated to APC (Jackson ImmunoResearch Laboratories, West Grove, Pa.) at 1:300 dilution. JeKo-1 and HBL-2 cell binding of dsFv-PE38 immunotoxin conjugates is detected using rabbit anti-*Pseudomonas* exotoxin A pAb (1:100 dilution) (Sigma-Aldrich, St. Louis, Mo.) as a secondary antibody and goat anti-rabbit IgG pAb conjugated to Cy5 (1:300 dilution) (Jackson ImmunoResearch Laboratories) as a tertiary antibody. The results are expected to demonstrate that, despite the inherent monovalency of a recombinant dsFv-PE38 immunotoxin, binding to native cell surface ROR1 is detectable at low concentrations.

An analysis of dsFv-PE38 immunotoxin binding to PBMC from B-CLL patients is expected to show similar results. Additionally, ELISA experiments are expected to demonstrate that dsFv-PE38 immunotoxin retains binding specificity for the extracellular domain of human ROR1.

The foregoing example provides a method of preparing a recombinant immunotoxin conjugated antibody of the invention, which is based on mAb R11, R12, or Y31, and which has conserved binding specificity for ROR1, including native ROR1 expressed on the cell surface of malignant B-cells.

Example 9

This example demonstrates cytotoxic properties of dsFv of chimeric rabbit/human anti-ROR1 antibodies R11, R12, and Y31 fused to an immunotoxin applied to ROR1 expressing cells.

JeKo-1 and HBL-2 cells are cultured in Roswell Park Memorial Institute (RPMI) 1640 medium supplemented with 10% fetal calf serum and incubated for 48 hours at 37° C. in a 96-well tissue culture plate with various doses (0-100 μg/mL) of the dsFv-PE38 immunotoxin prepared in Example 8. The cells are subsequently analyzed by flow cytometry using annexin V and propidium iodide to stain apoptotic and dead cells, respectively. The percentage of cells positive for both annexin V and propidium iodide are evaluated as a function of the concentration of dsFv-PE38. The cytotoxicity of dsFv-PE38 includes not only cell death (necrosis) as evidenced by propidium iodide staining, but also extensive apoptosis, as evidenced by annexin V staining.

The foregoing example provides a method of evaluating the ability of a recombinant immunotoxin conjugated antibody of the invention, which is based on mAb R11, R12, or Y31, to effect dose-dependent killing of JeKo-1 and HBL-2 cells at low concentrations.

Example 10

This example demonstrates the ability of IgG1 R11, R12, and Y31 to induce or inhibit apoptosis in primary CLL cells from patients.

Apoptosis was evaluated in the presence and absence of fetal bovine serum (FBS). FBS has been shown to enhance spontaneous apoptosis of primary CLL cells ex vivo (Levesque et al., Leukemia, 15: 1305-1307 (2001)). Using FBS-free medium, apoptosis induction was analyzed in PBMC from three CLL patients with 80% or more CD19+ CD5+ROR1+ cells following incubation for three days with IgG1 R11, R12, Y31, TT11, and rituximab alone or in the presence of a cross-linking pAb. PBMC from CLL patients were distributed into 48-well flat-bottom plates at a density of $5 \times 10^5$ cells/well in either (i) serum-free AIM-V medium (Invitrogen) supplemented with 50 μM β-mercaptoethanol (Sigma-Aldrich) or (ii) RPMI 1640 supplemented with 10% (v/v) heat-inactivated fetal bovine serum, 100 U/mL penicillin, and 100 μg/mL streptomycin in the presence or absence of 100 ng/mL recombinant human IL-4 (R&D Systems) and 1 μg/mL soluble recombinant human CD40L trimer (Amgen, Thousand Oaks, Calif.). Cells were incubated with 5 μg/mL IgG1 R11, R12, Y31, TT11, or rituximab at 37° C. in 5% $CO_2$. For cross-linking, 20 μg/mL $F(ab')_2$ goat anti-human IgG (Fc-specific, Jackson ImmunoResearch Laboratories) was added to the cell suspension simultaneously with primary antibodies. Apoptosis and cell death was measured by flow cytometry following staining with Alexa Fluor 647 Annexin V (Invitrogen) and SYTOX Green nucleic acid stain (Invitrogen). Briefly, cells were gently harvested after 72 h incubation with indicated treatments, washed once with cold apoptosis binding buffer (140 mM NaCl, 2.5 mM $CaCl_2$, 10 mM HEPES, pH 7.4), and resuspended in 200 μL apoptosis binding buffer. After adding 1 μL Alexa Fluor 647 Annexin V and 1 μL SYTOX Green to a final concentration of 50 nM, the cells were incubated for 15 min in the dark at room temperature, resuspended in 400 μL apoptosis binding buffer, and analyzed using a FACSCalibur instrument and FlowJo analytical software.

As shown in FIG. 11A, the only increase in spontaneous apoptosis was noted for cross-linked rituximab. This was consistent and reproducible for all three tested PBMC samples. In the presence of FBS, apoptosis approached 50% after three days (FIG. 11B). As observed previously, the addition of IL-4 and CD40L strongly suppressed apoptosis. See, e.g., Baskar et al., *Clin. Cancer Res.*, 14: 396-404 (2008). IgG1 R11, R12, Y31, and TT11 (negative control) neither increased nor decreased apoptosis alone or after cross-linking. They also did not influence the suppression of apoptosis by IL-4 and CD40L. By contrast, cross-linked rituximab was found to increase apoptosis and partially override its suppression (FIG. 11B).

The induction of apoptosis in MCL cell line HBL-2 also was investigated (data not shown). In contrast to primary CLL cells, rituximab alone was sufficient to induce apoptosis in HBL-2 cells. This activity was further increased after cross-linking. Nonetheless, IgG1 R11, R12, and Y31 did not induce apoptosis in HBL-2 cells with or without cross-linking.

These results demonstrate that this panel of chimeric rabbit/human IgG1 antibodies neither induces nor inhibits apoptosis of primary CLL cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antibody having specificity for the extracellular domain of human receptor tyrosine kinase-like orphan receptor 1 (ROR1), comprising complementarity-determining regions (CDRs) with the following sequences:
   (a) SEQ ID NO: 31 as light chain CDR1 (LCDR1), SEQ ID NO: 32 as LCDR2, SEQ ID NO: 33 as LCDR3, SEQ ID NO: 40 as heavy chain CDR1 (HCDR1), SEQ ID NO: 41 as HCDR2, and SEQ ID NO: 42 as HCDR3,
   (b) SEQ ID NO: 34 as LCDR1, SEQ ID NO: 35 as LCDR2, SEQ ID NO: 36 as LCDR3, SEQ ID NO: 43 as HCDR1, SEQ ID NO: 42 as HCDR2, and SEQ ID NO: 43 as HCDR3, or
   (c) SEQ ID NO: 37 as LCDR1, SEQ ID NO: 38 as LCDR2, SEQ ID NO: 39 as LCDR3, SEQ ID NO: 46 as HCDR1, SEQ ID NO: 47 as HCDR2, and SEQ ID NO: 48 as HCDR3.

2. The antibody of claim 1, wherein the antibody comprises
   (a) a light chain variable domain having at least 95% sequence identity to the amino acid sequence of SEQ ID NO: 1 and a heavy chain variable domain having at least 95% sequence identity to the amino acid sequence of SEQ ID NO: 2,
   (b) a light chain variable domain having at least 95% sequence identity to the amino acid sequence of SEQ ID NO: 3 and a heavy chain variable domain having at least 95% sequence identity to the amino acid sequence of SEQ ID NO: 4, or
   (c) a light chain variable domain having at least 95% sequence identity to the amino acid sequence of SEQ ID NO: 5 and a heavy chain variable domain having at least 95% sequence identity to the amino acid sequence of SEQ ID NO: 6.

3. The antibody of claim 2, wherein
(a) the light chain variable domain comprises the amino acid sequence of SEQ ID NO: 1 and the heavy chain variable domain comprises the amino acid sequence of SEQ ID NO: 2;
(b) the light chain variable domain comprises the amino acid sequence of SEQ ID NO: 3 and the heavy chain variable domain comprises the amino acid sequence of SEQ ID NO: 4; or
(c) the light chain variable domain comprises the amino acid sequence of SEQ ID NO: 5 and the heavy chain variable domain comprises the amino acid sequence of SEQ ID NO: 6.

4. The antibody of claim 1, wherein the light chain variable domain consists of the amino acid sequence of SEQ ID NO: 1 and the heavy chain variable domain consists of the amino acid sequence of SEQ ID NO: 2.

5. The antibody of claim 1, wherein the light chain variable domain consists of the amino acid sequence of SEQ ID NO: 3 and the heavy chain variable domain consists of the amino acid sequence of SEQ ID NO: 4.

6. The antibody of claim 1, wherein the light chain variable domain consists of the amino acid sequence of SEQ ID NO: 5 and the heavy chain variable domain consists of the amino acid sequence of SEQ ID NO: 6.

7. The antibody of claim 1, wherein the antibody is conjugated to a synthetic molecule.

8. The antibody of claim 7, wherein the synthetic molecule comprises a transmembrane region and an intracellular T-cell receptor (TCR) signaling domain.

9. The antibody of claim 7, wherein the synthetic molecule is a label, cytotoxic agent, a therapeutic radioisotope, or a liposome.

10. The antibody of claim 9, wherein the cytotoxic agent is a toxin.

11. The antibody of claim 7, wherein the synthetic molecule is another antibody.

12. The antibody of claim 11, wherein the synthetic molecule is rituximab or bevacuzimab.

13. A pharmaceutical composition comprising a therapeutically effective amount of an isolated antibody of claim 1 and a pharmaceutically acceptable carrier.

14. A kit comprising the isolated antibody of claim 1.

15. The kit of claim 14, further comprising one or more immunoassay buffers.

16. The antibody of claim 1, comprising the following CDR sequences: SEQ ID NO: 31 as LCDR1, SEQ ID NO: 32 as LCDR2, SEQ ID NO: 33 as LCDR3, SEQ ID NO: 40 as HCDR1, SEQ ID NO: 41 as HCDR2, and SEQ ID NO: 42 as HCDR3.

17. The antibody of claim 1, wherein the antibody is a humanized antibody.

18. A conjugate comprising the antibody of claim 1 and a cytotoxic agent.

19. The conjugate of claim 18, wherein the cytotoxic agent is a toxin.

20. The conjugate of claim 19, wherein the toxin is a fragment of *Pseudomonas* exotoxin A (PE).

21. The conjugate of claim 20, wherein the fragment of PE is PE38.

22. The antibody of claim 1, comprising the following CDR sequences: SEQ ID NO: 34 as LCDR1, SEQ ID NO: 35 as LCDR2, SEQ ID NO: 36 as LCDR3, SEQ ID NO: 43 as HCDR1, SEQ ID NO: 42 as HCDR2, and SEQ ID NO: 43 as HCDR3.

23. The antibody of claim 1, comprising the following CDR sequences: SEQ ID NO: 37 as LCDR1, SEQ ID NO: 38 as LCDR2, SEQ ID NO: 39 as LCDR3, SEQ ID NO: 46 as HCDR1, SEQ ID NO: 47 as HCDR2, and SEQ ID NO: 48 as HCDR3.

\* \* \* \* \*

UNITED STATES PATENT AND TRADEMARK OFFICE
CERTIFICATE OF CORRECTION

PATENT NO. : 9,758,586 B2
APPLICATION NO. : 13/990977
DATED : September 12, 2017
INVENTOR(S) : Rader et al.

It is certified that error appears in the above-identified patent and that said Letters Patent is hereby corrected as shown below:

In the Claims

In Claim 1, Column 45, Lines 62-63, change "SEQ ID NO: 42 as HCDR2, and SEQ ID NO: 43 as HCDR3" to --SEQ ID NO: 44 as HCDR2, and SEQ ID NO: 45 as HCDR3--

In Claim 22, Column 48, Lines 30-31, change "SEQ ID NO: 42 as HCDR2, and SEQ ID NO: 43 as HCDR3" to --SEQ ID NO: 44 as HCDR2, and SEQ ID NO: 45 as HCDR3--

Signed and Sealed this
Tenth Day of July, 2018

Andrei Iancu
*Director of the United States Patent and Trademark Office*